US010281678B2

(12) United States Patent
Chamberlin et al.

(10) Patent No.: US 10,281,678 B2
(45) Date of Patent: May 7, 2019

(54) ASSAY APPARATUSES, METHODS AND REAGANTS

(71) Applicant: Meso Scale Technologies, LLC, Gaithersburg, MD (US)

(72) Inventors: Ian Chamberlin, Burtonsville, MD (US); Charles M. Clinton, Clarksburg, MD (US); Eli N. Glezer, Del Mar, CA (US); Bandele Jeffrey-Coker, Darnestown, MD (US); Manish Kochar, Rockville, MD (US); Sandor Kovacs, Middletown, DE (US); D. T. Le, Beltsville, MD (US); Aaron Leimkuehler, Pittsburg, PA (US); George Sigal, Rockville, MD (US); Leo Tabakin, Germantown, MD (US); Jon Willoughby, Potomac, MD (US)

(73) Assignee: Meso Scale Technologies, LLC, Gaithersburg, MD (US)

( * ) Notice: Subject to any disclaimer, the term of this patent is extended or adjusted under 35 U.S.C. 154(b) by 451 days.

(21) Appl. No.: 14/147,216

(22) Filed: Jan. 3, 2014

(65) Prior Publication Data

US 2014/0191109 A1    Jul. 10, 2014

Related U.S. Application Data

(60) Provisional application No. 61/749,097, filed on Jan. 4, 2013.

(51) Int. Cl.
*G02B 7/36* (2006.01)
*G01N 35/02* (2006.01)
(Continued)

(52) U.S. Cl.
CPC .............. *G02B 7/36* (2013.01); *G01N 21/253* (2013.01); *G01N 21/6452* (2013.01); *G01N 35/028* (2013.01)

(58) Field of Classification Search
CPC .. G02B 7/36; G02B 7/38; G01N 27/26; G01J 1/20
See application file for complete search history.

(56) References Cited

U.S. PATENT DOCUMENTS 5,432,086 A * 7/1995 Franzl .............. G01N 33/48735
324/447
5,643,742 A * 7/1997 Malin ................ G01N 33/5011
324/692
(Continued)

FOREIGN PATENT DOCUMENTS

WO        9115595 A1    10/1991
WO        96/28538 A1    9/1996
(Continued)

OTHER PUBLICATIONS

International Search Report and Written Opinion issued in connection with the corresponding International Application No. PCT/US2014/010182 dated Jun. 17, 2014.
(Continued)

*Primary Examiner* — Georgia Y Epps
*Assistant Examiner* — Don Williams
(74) *Attorney, Agent, or Firm* — The H.T. Than Law Group

(57) ABSTRACT

Apparatuses, systems, method, reagents, and kits for conducting assays as well as process for their preparation are described. They are particularly well suited for conducting automated analysis in a multi-well plate assay format.

28 Claims, 36 Drawing Sheets

(51) Int. Cl.
*G01N 21/25* (2006.01)
*G01N 21/64* (2006.01)

(56) References Cited

U.S. PATENT DOCUMENTS

| | | | |
|---|---|---|---|
| 5,966,208 | A | 10/1999 | Samuelson |
| 6,002,426 | A * | 12/1999 | Back ................ H04N 7/181 |
| | | | 324/750.23 |
| 6,207,369 | B1 | 3/2001 | Wohlstadter |
| 6,235,520 | B1 | 5/2001 | Malin et al. |
| 7,842,246 | B2 | 11/2010 | Wohlstadter et al. |
| 8,173,332 | B2 | 5/2012 | Kamo et al. |
| 2004/0022677 | A1 | 2/2004 | Wohlstadter et al. |
| 2004/0022689 | A1 | 2/2004 | Wulf et al. |
| 2004/0252195 | A1 | 12/2004 | Lu et al. |
| 2005/0048651 | A1 | 3/2005 | Ryttsen et al. |
| 2005/0196776 | A1 * | 9/2005 | Yang ................ G01N 27/3277 |
| | | | 435/6.12 |
| 2005/0247559 | A1 | 11/2005 | Frey et al. |
| 2005/0250173 | A1 * | 11/2005 | Davis ................ G01N 35/028 |
| | | | 435/29 |
| 2006/0023213 | A1 * | 2/2006 | Funakubo ......... G01N 21/1717 |
| | | | 356/369 |
| 2006/0038976 | A1 | 2/2006 | Knoedgen et al. |
| 2006/0216203 | A1 * | 9/2006 | Fuller ................ B01L 3/5085 |
| | | | 422/82.01 |
| 2006/0249558 | A1 * | 11/2006 | Roach ................ G01N 35/04 |
| | | | 228/101 |
| 2007/0058159 | A1 | 3/2007 | Greve et al. |
| 2007/0231217 | A1 | 10/2007 | Clinton et al. |
| 2008/0264170 | A1 | 10/2008 | Abbott |
| 2011/0256630 | A1 | 10/2011 | Clinton |

FOREIGN PATENT DOCUMENTS

| | | |
|---|---|---|
| WO | 9749987 A1 | 12/1997 |
| WO | 2007039783 A2 | 4/2007 |
| WO | 2009126303 A2 | 10/2009 |

OTHER PUBLICATIONS

European Search Report issued in connection with the corresponding European Patent Application No. 14735206.6 dated Jul. 7, 2016.
Extended European Search Report issued in connection with corresponding the European Patent Application No. 14735206.6 dated Nov. 4, 2016.
Australian Search Report issued in connection with the corresponding Australian patent application No. 2018204428 dated Dec. 21, 2018.

* cited by examiner

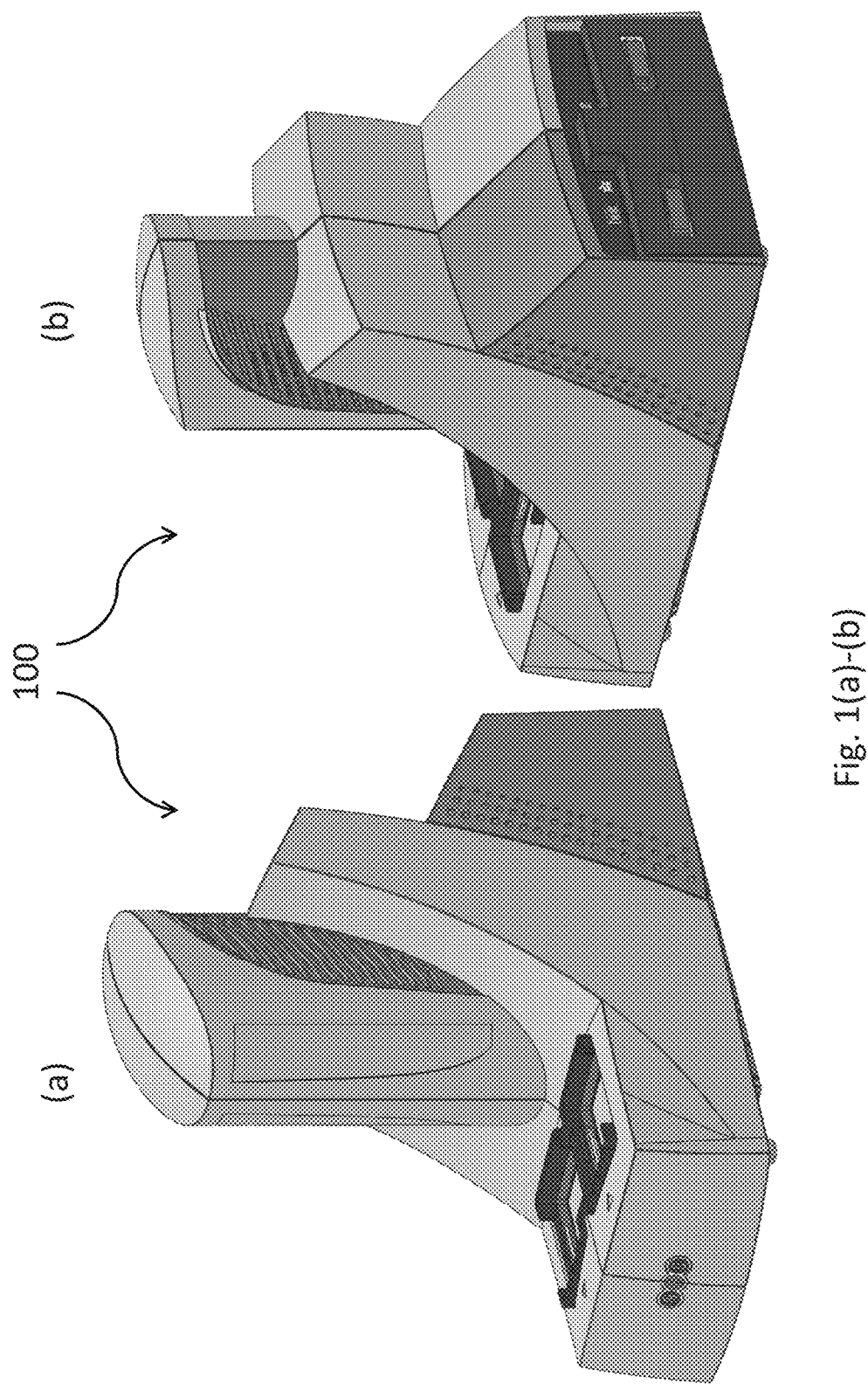
Fig. 1(a)-(b)

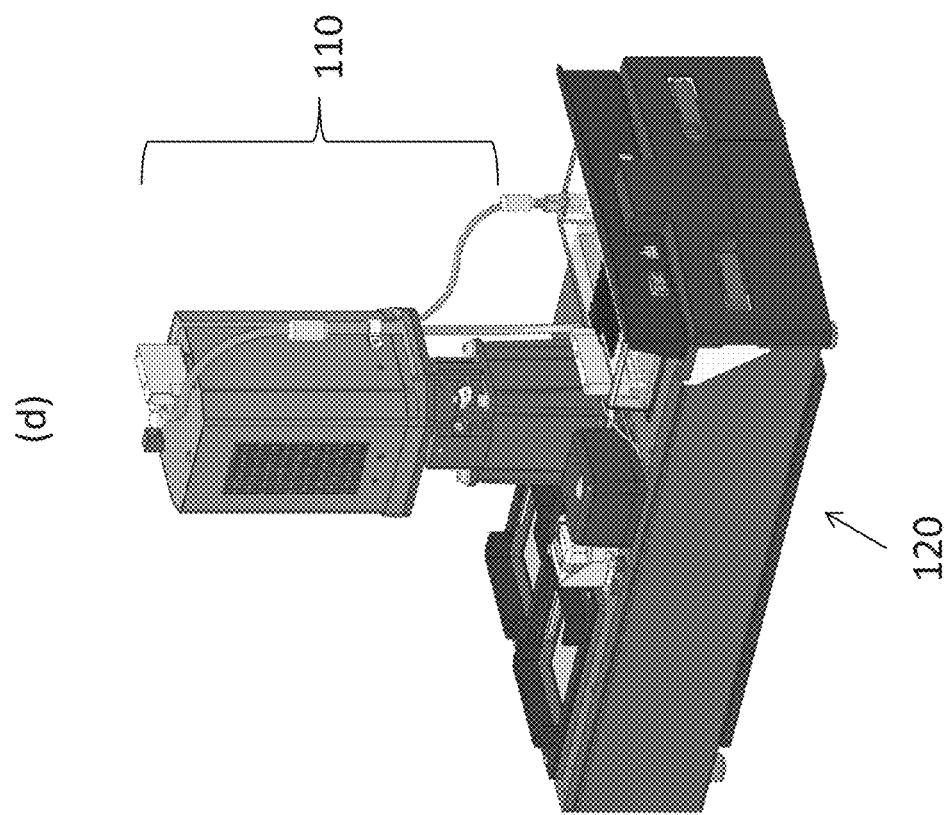
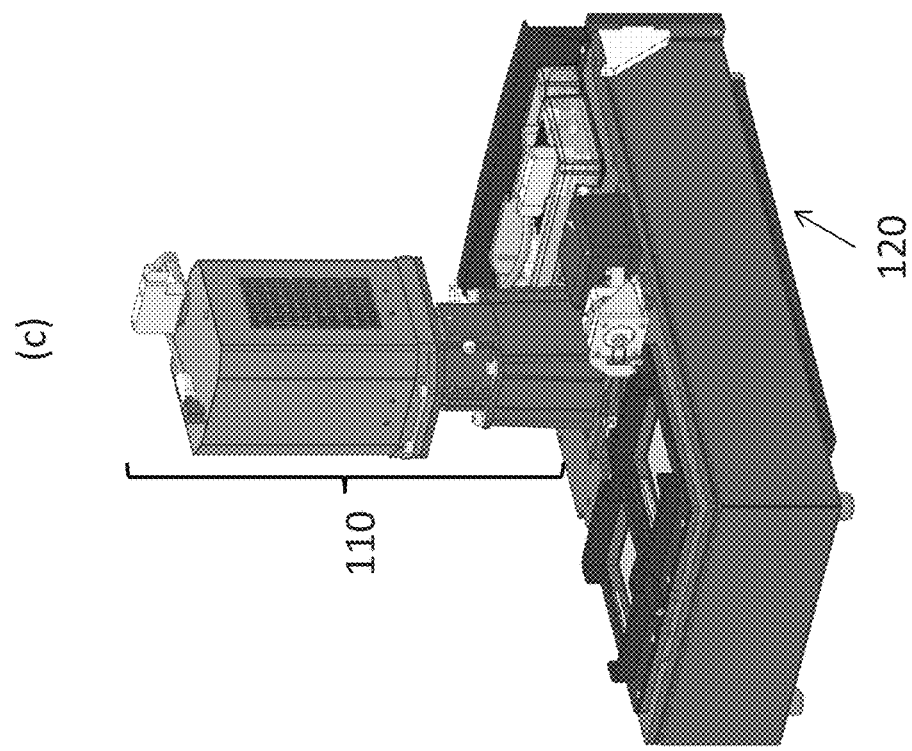
Fig. 1(c)-(d)

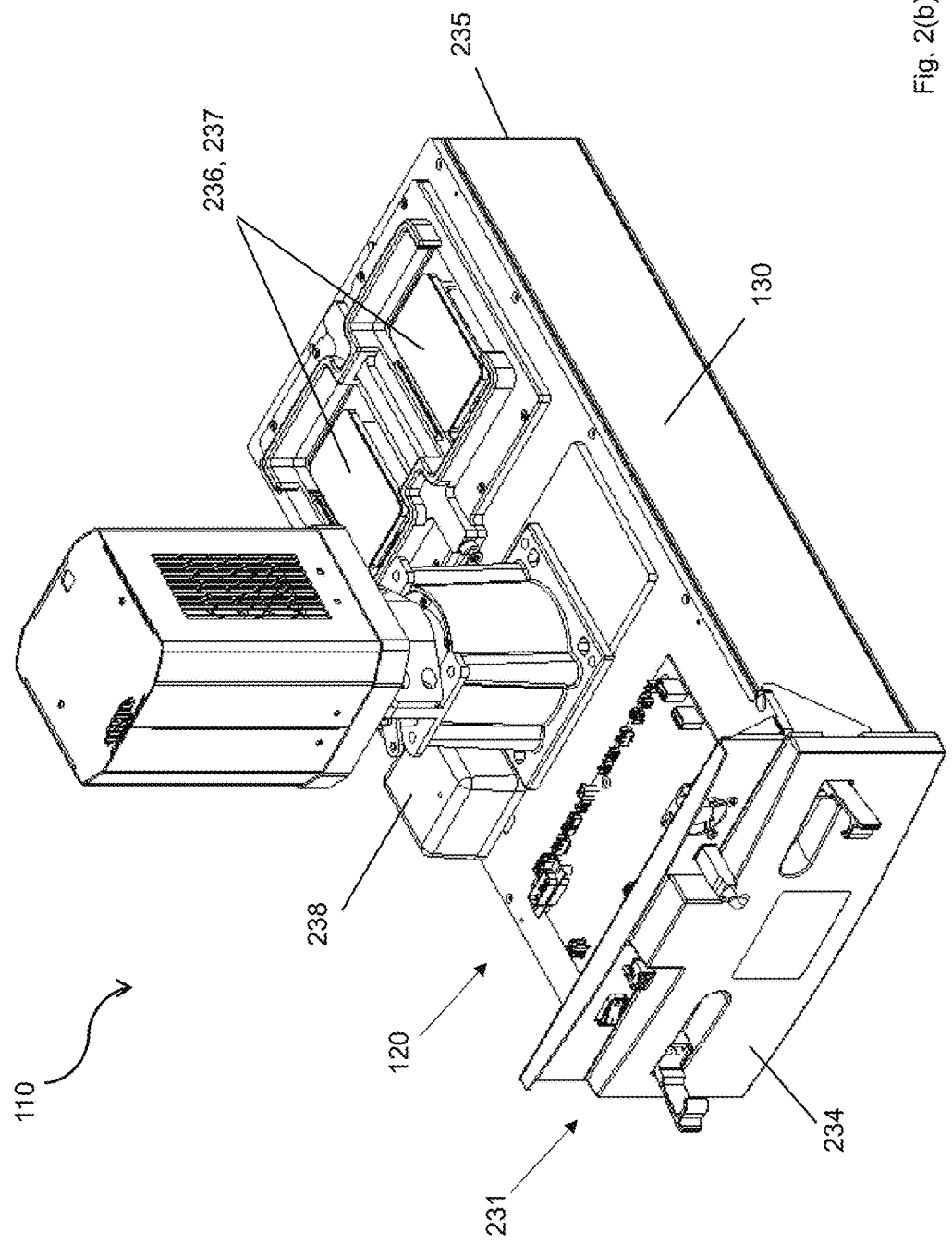

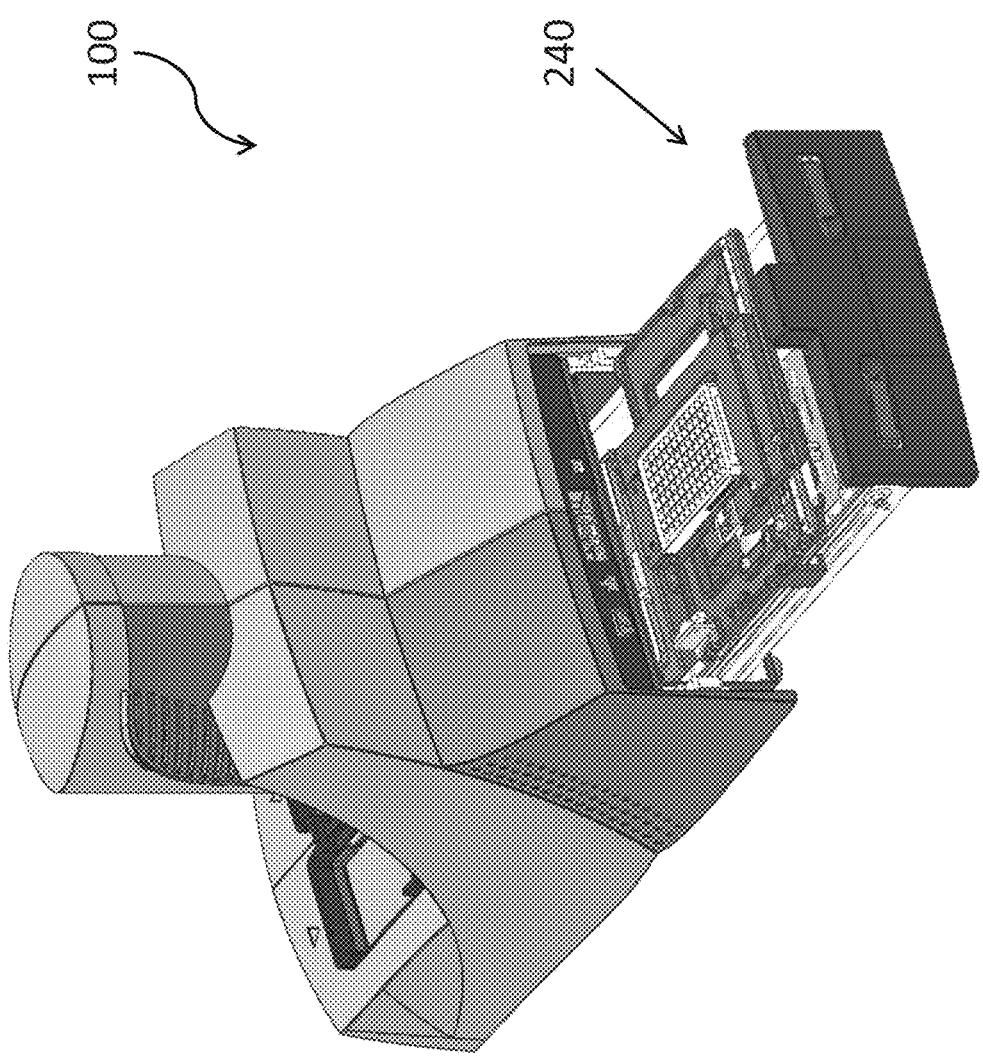

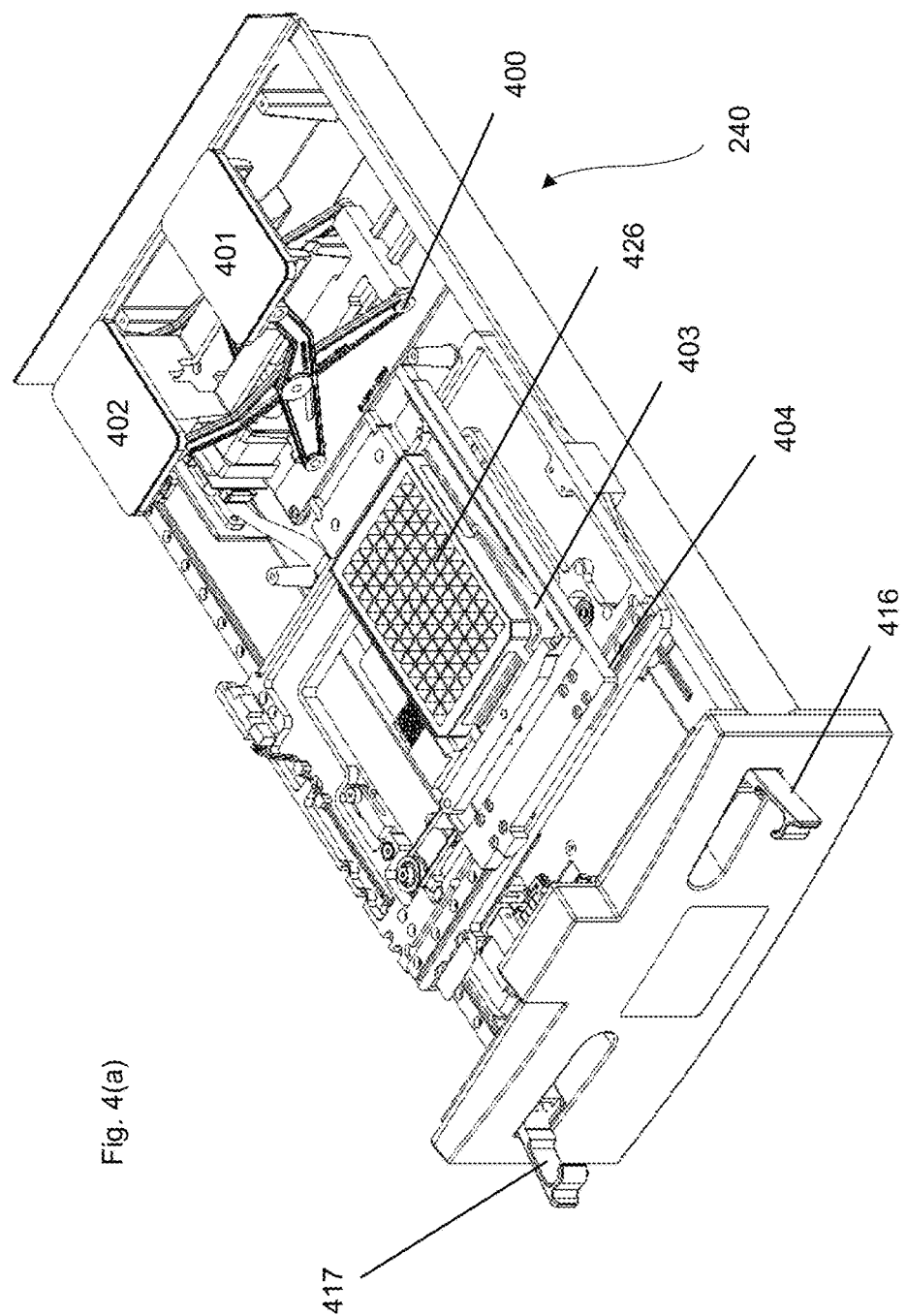

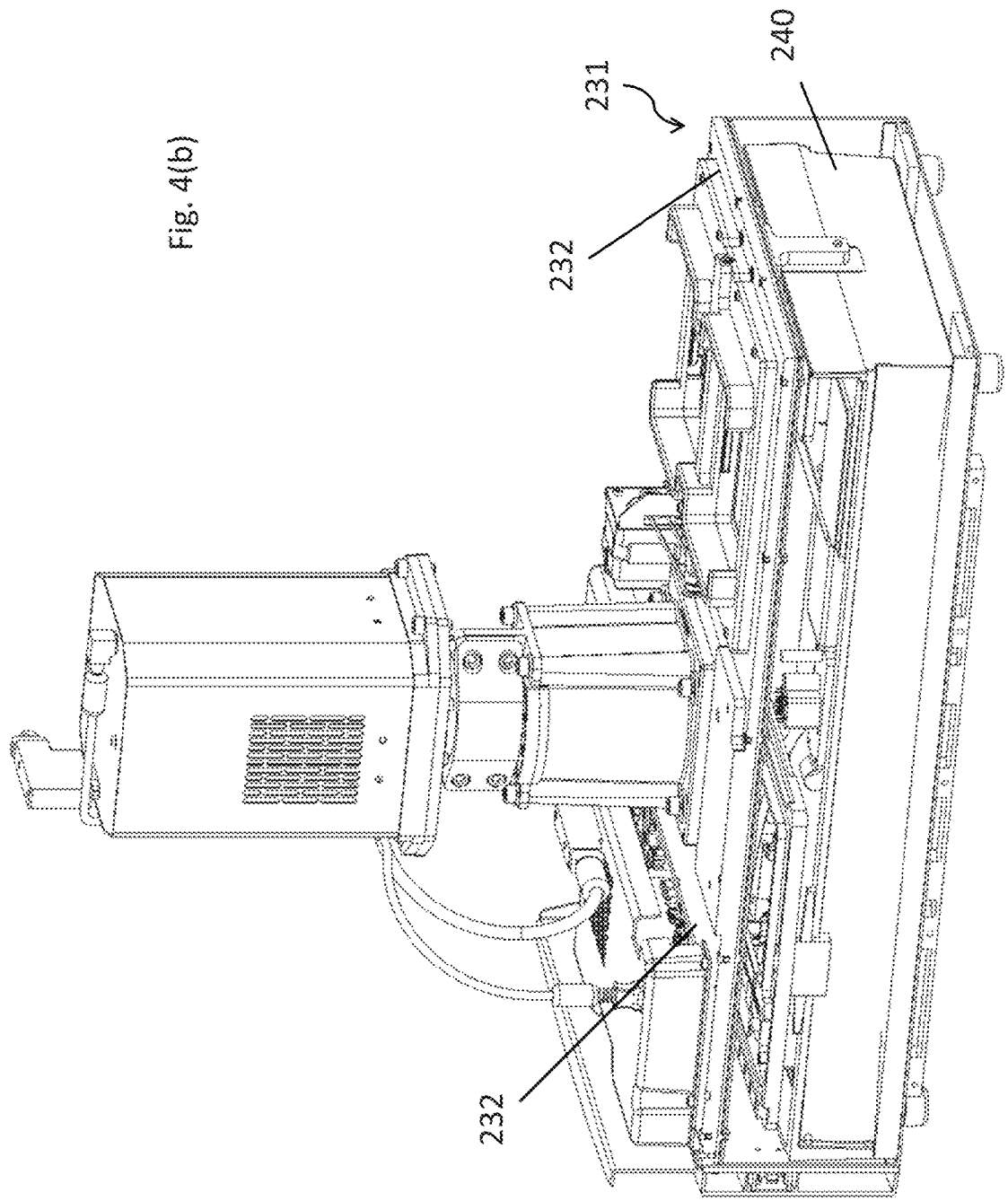

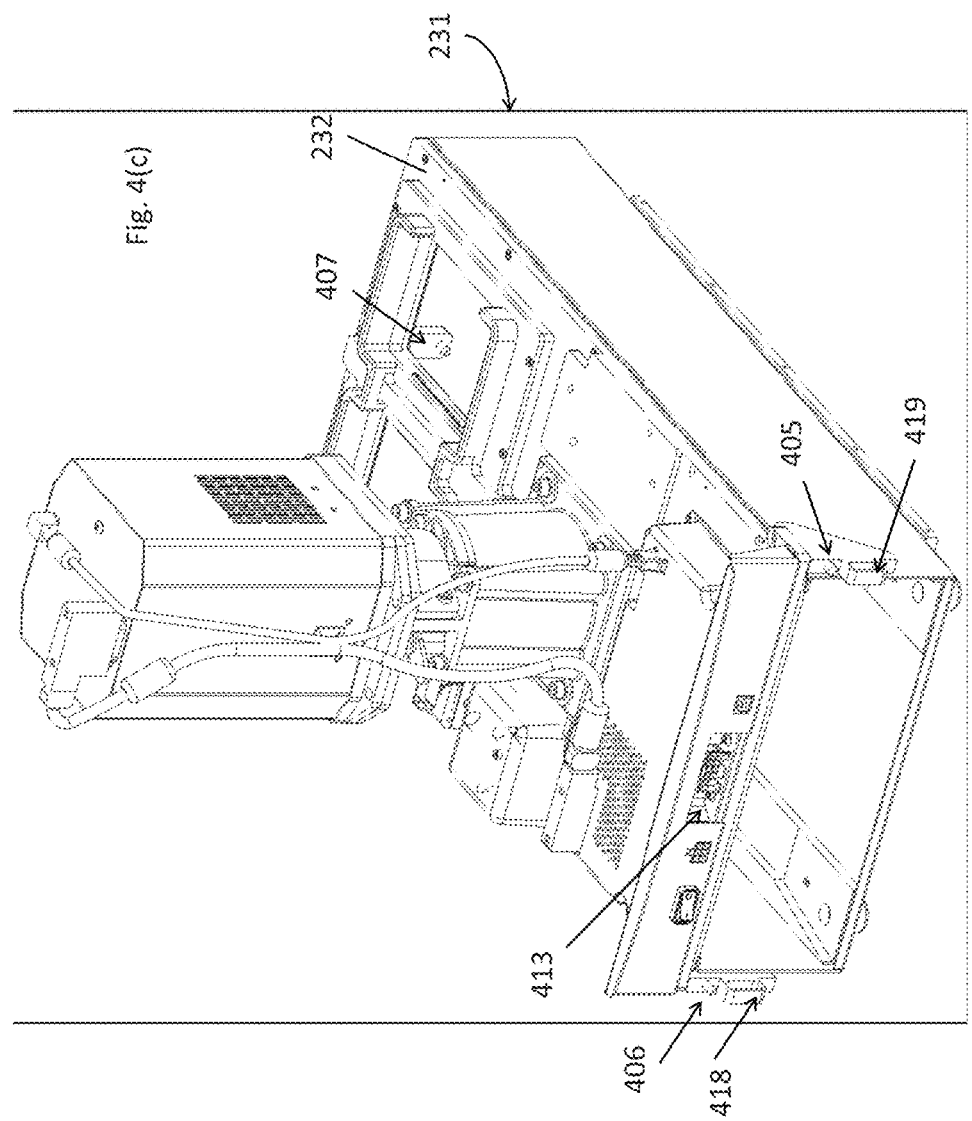

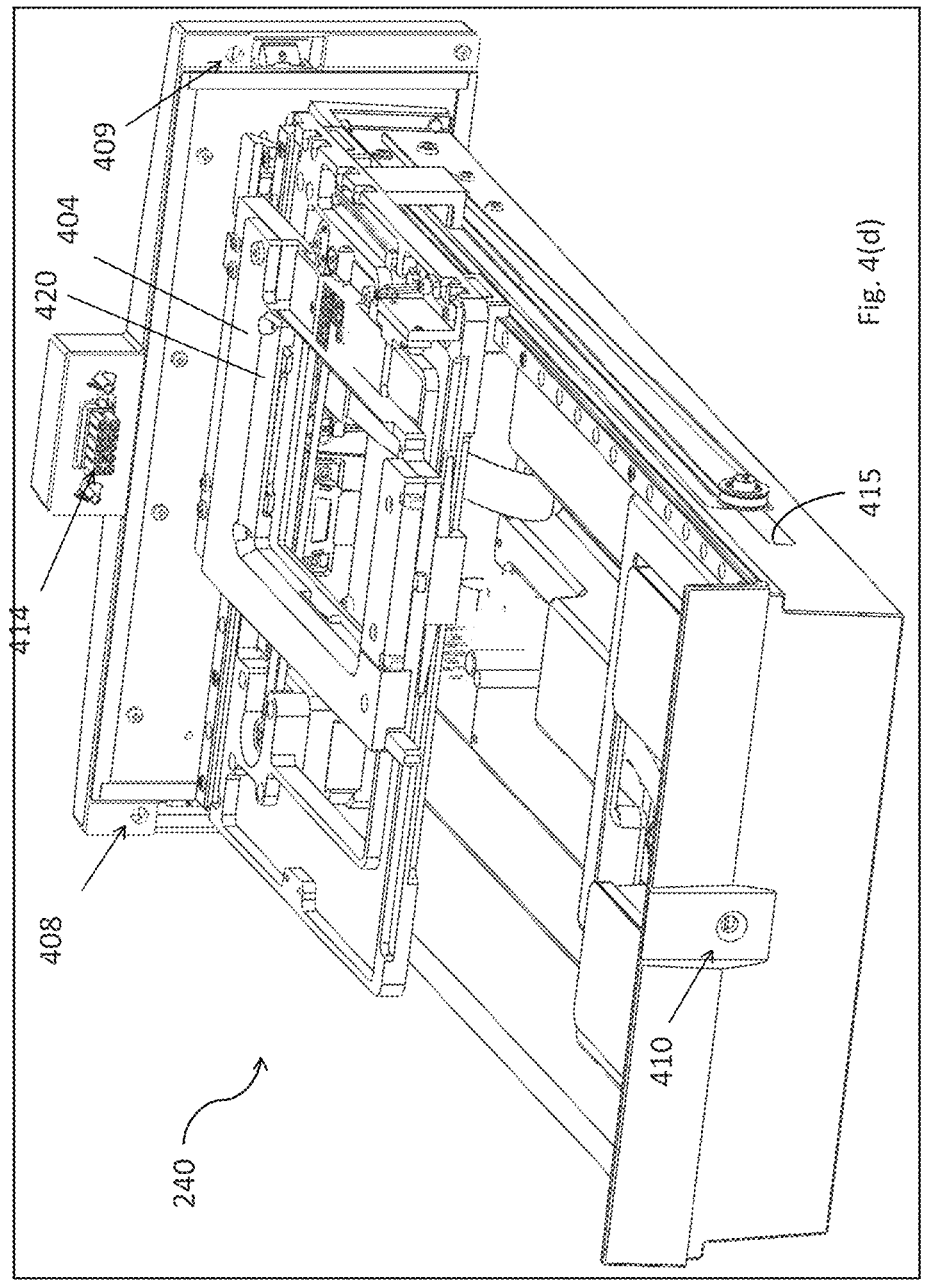

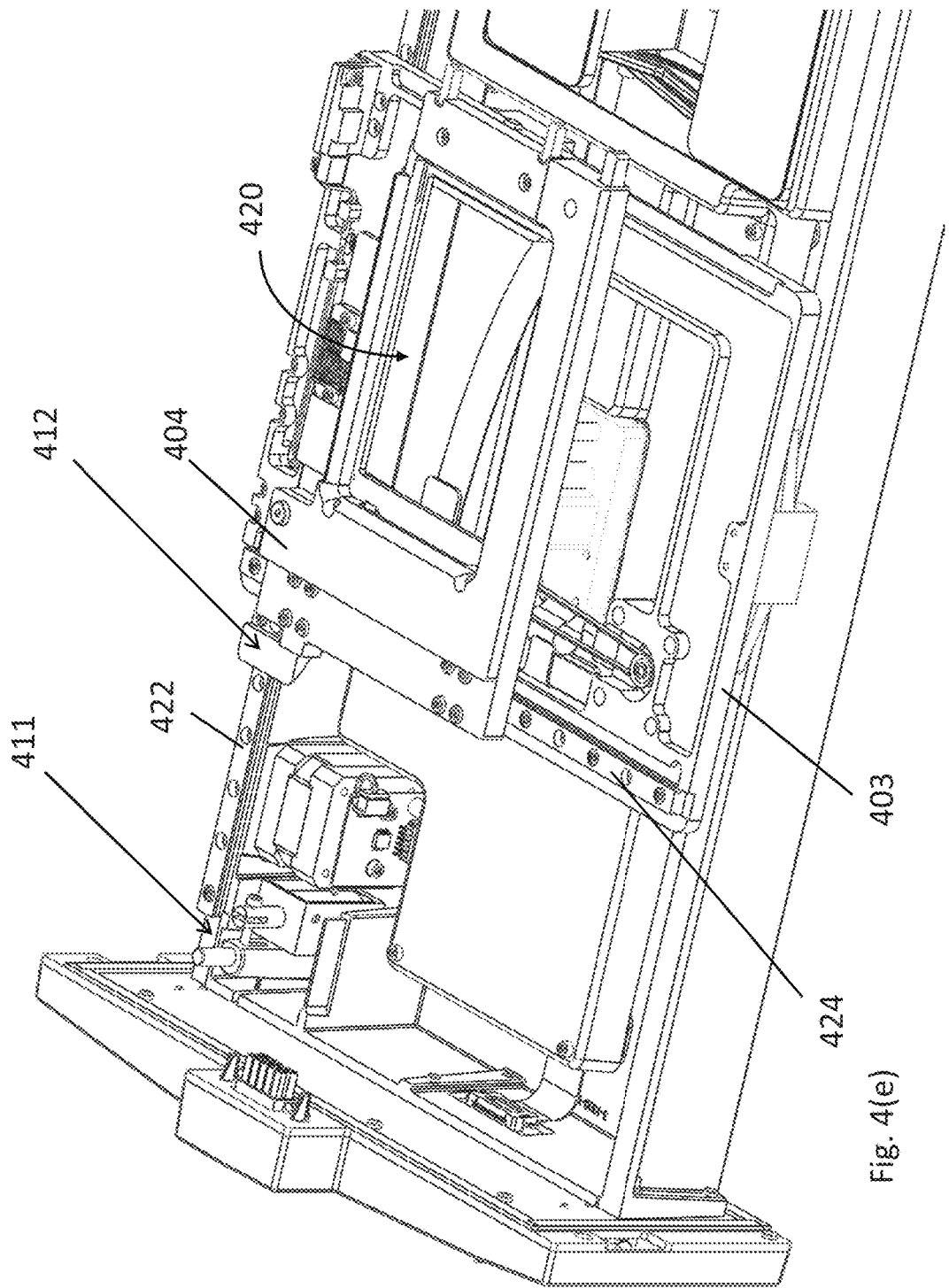

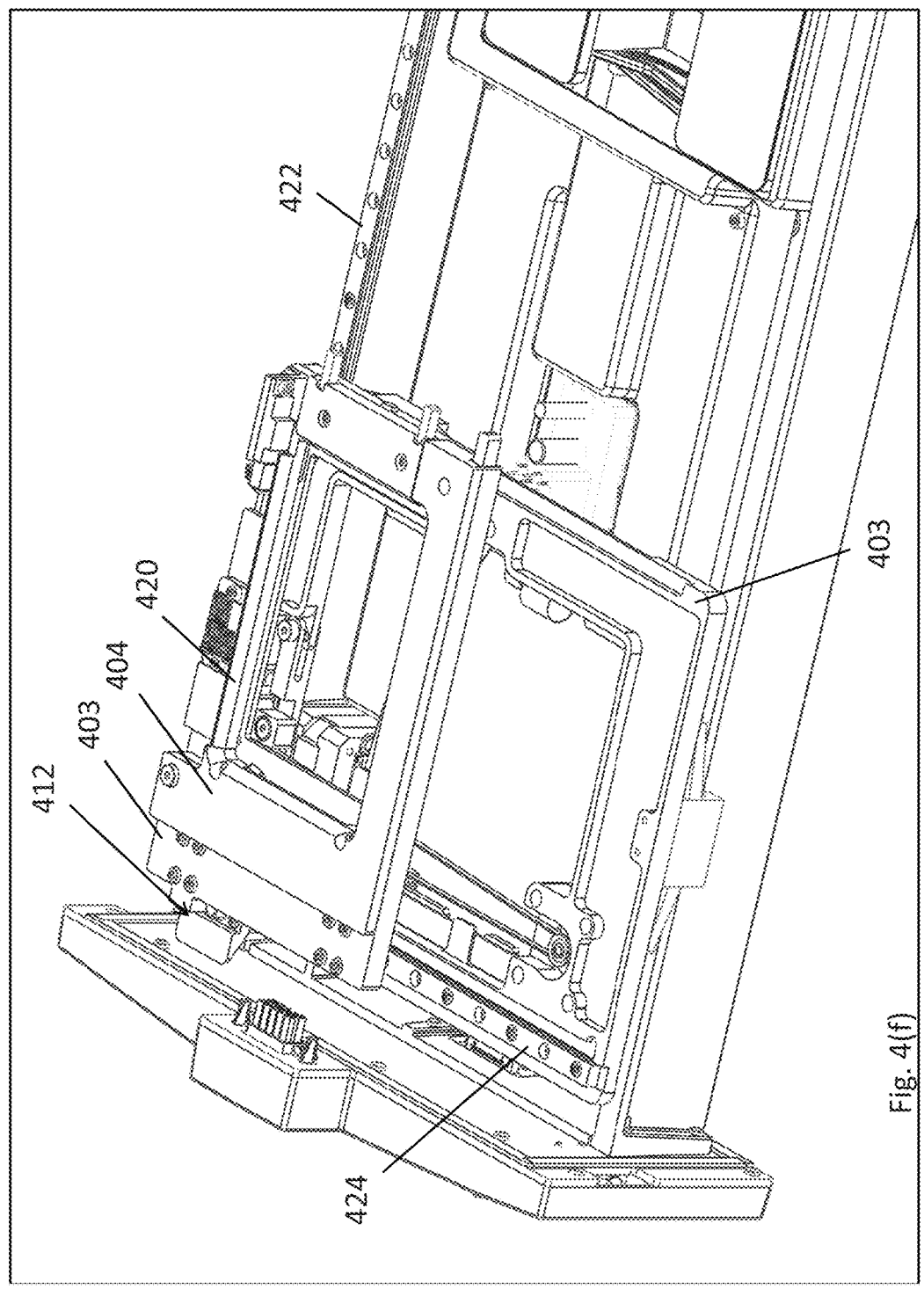

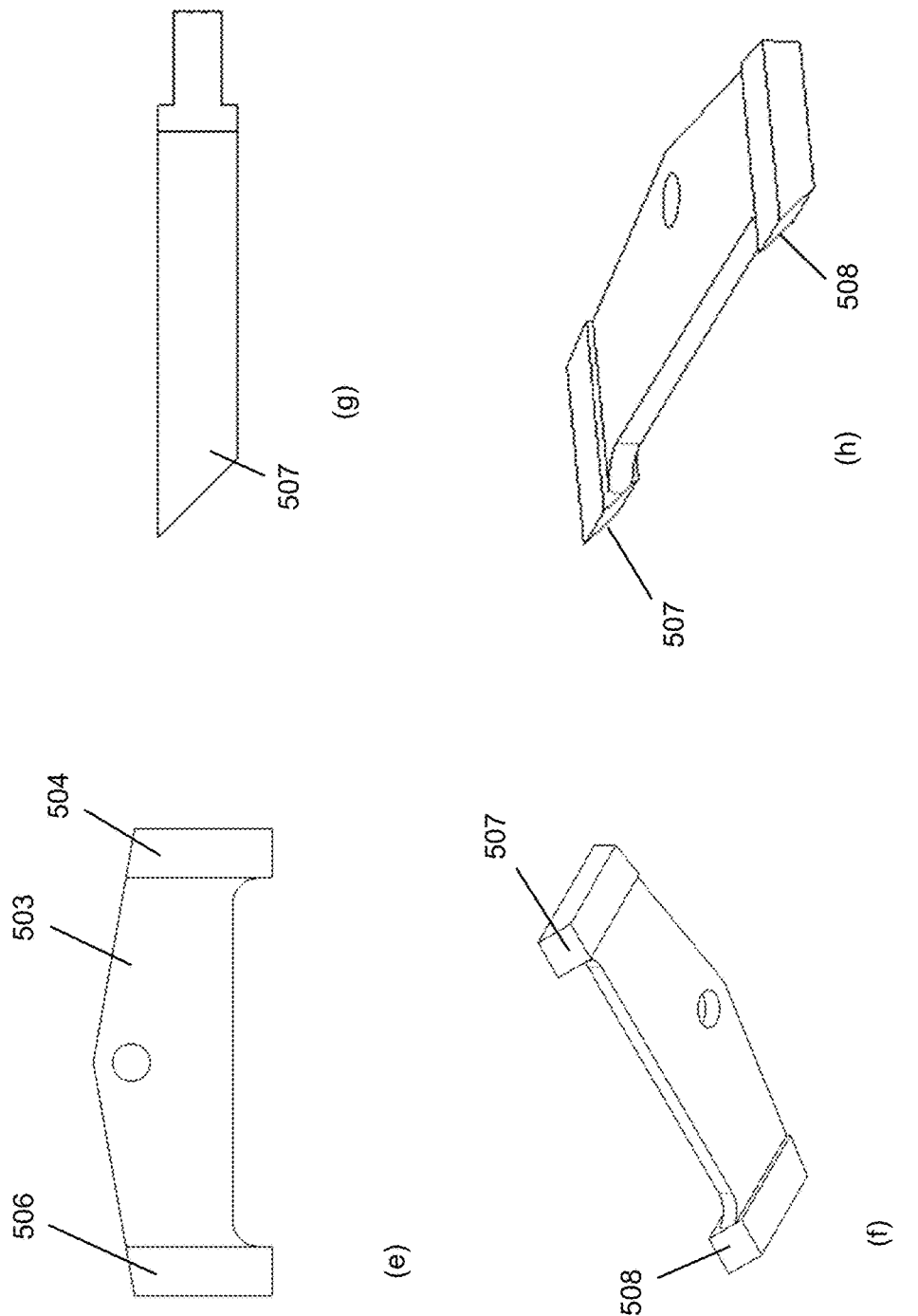
Fig. 5(e)-(h)

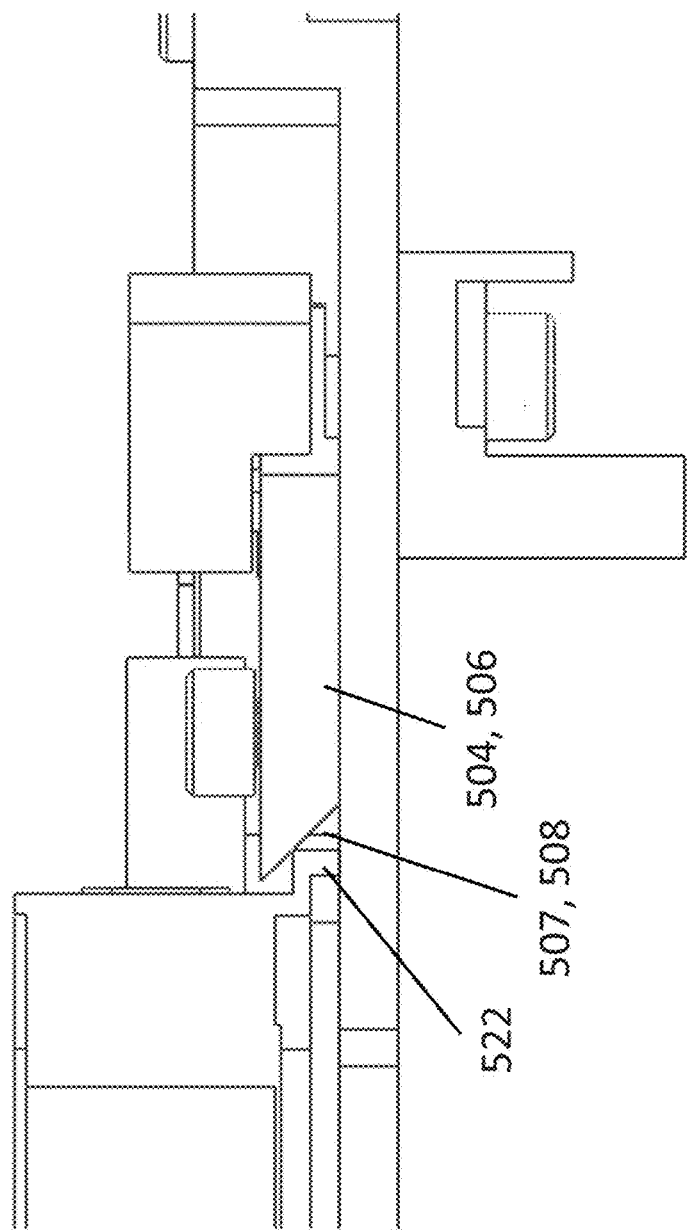

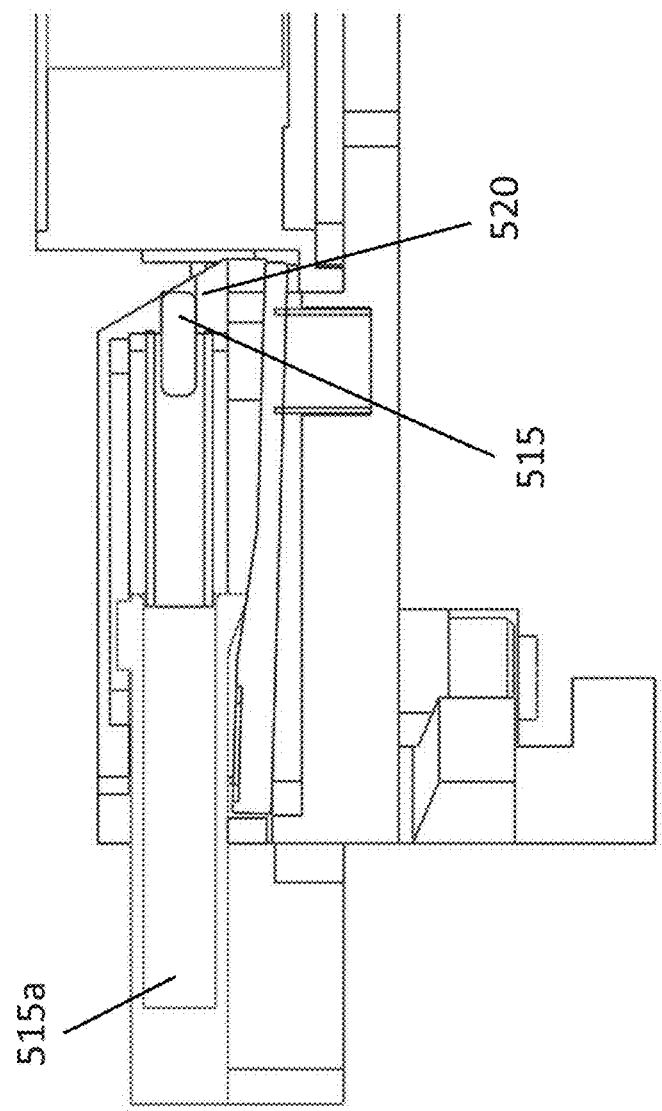

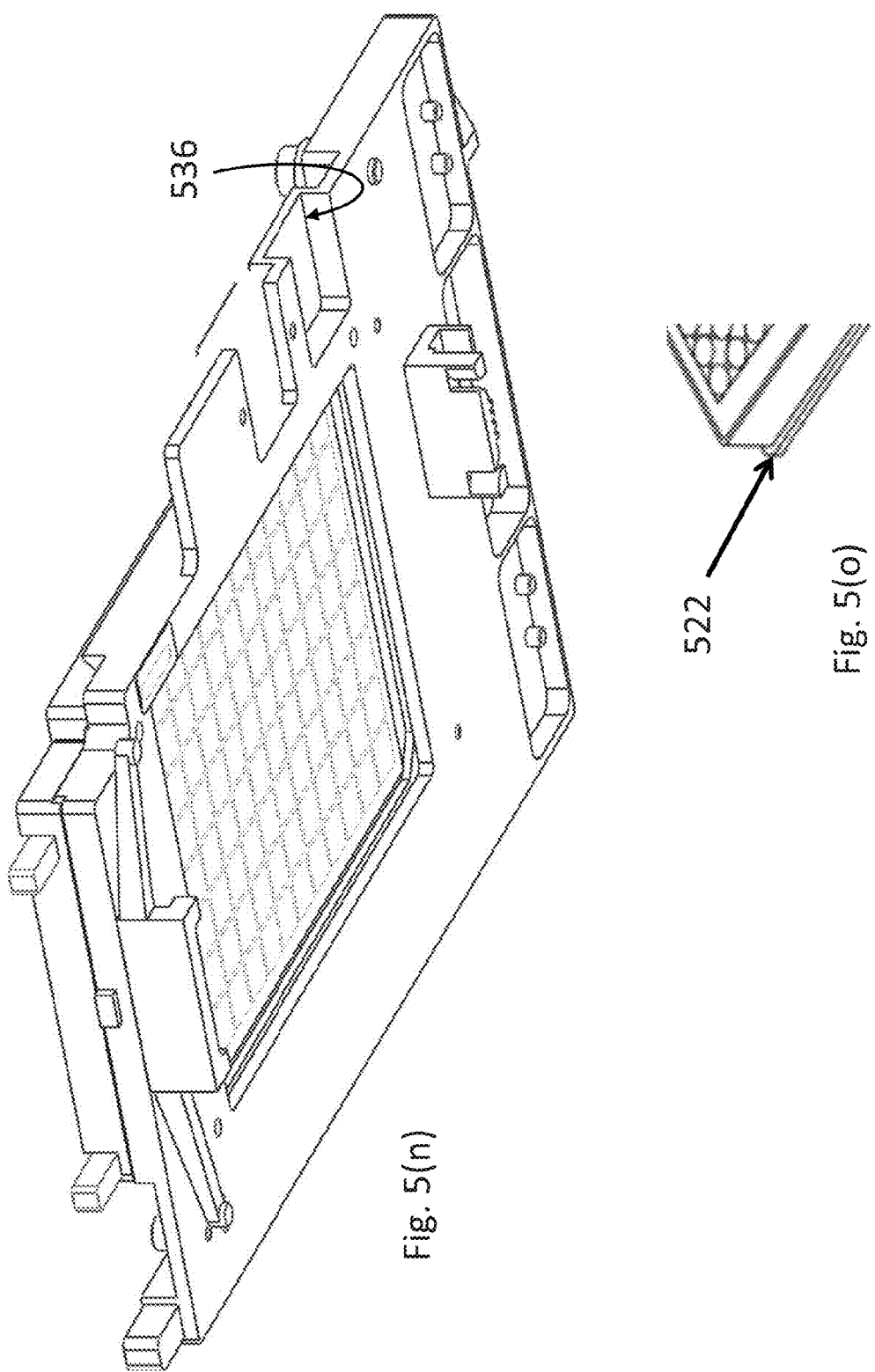

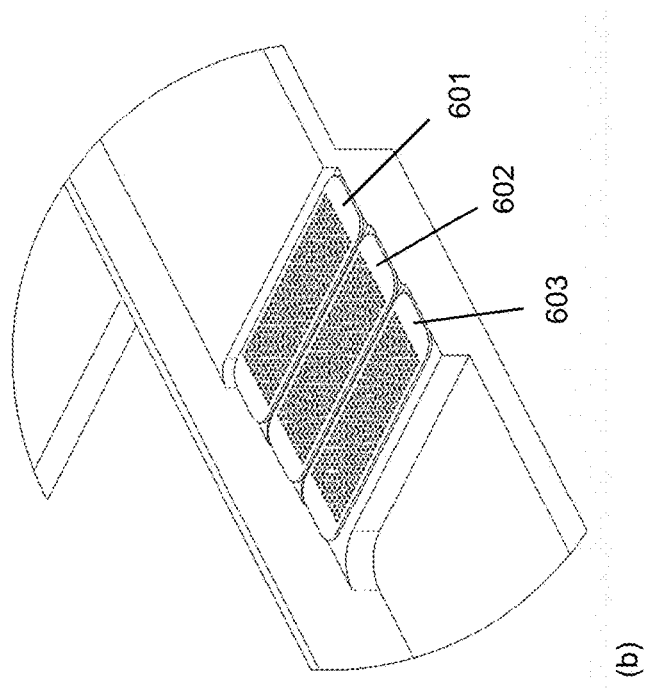
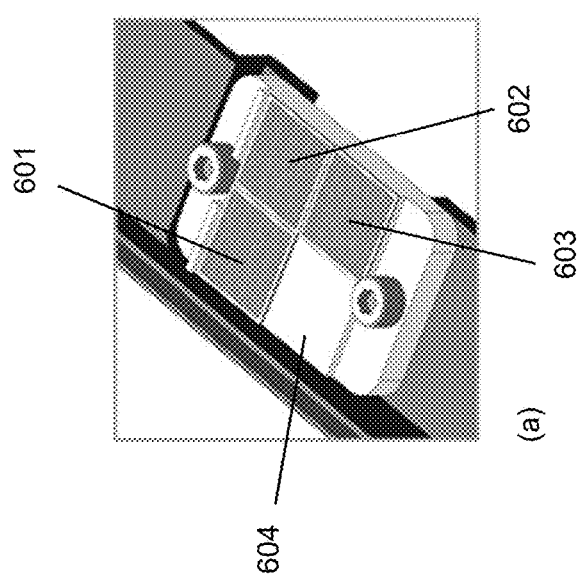
Fig. 6(a)-(b)

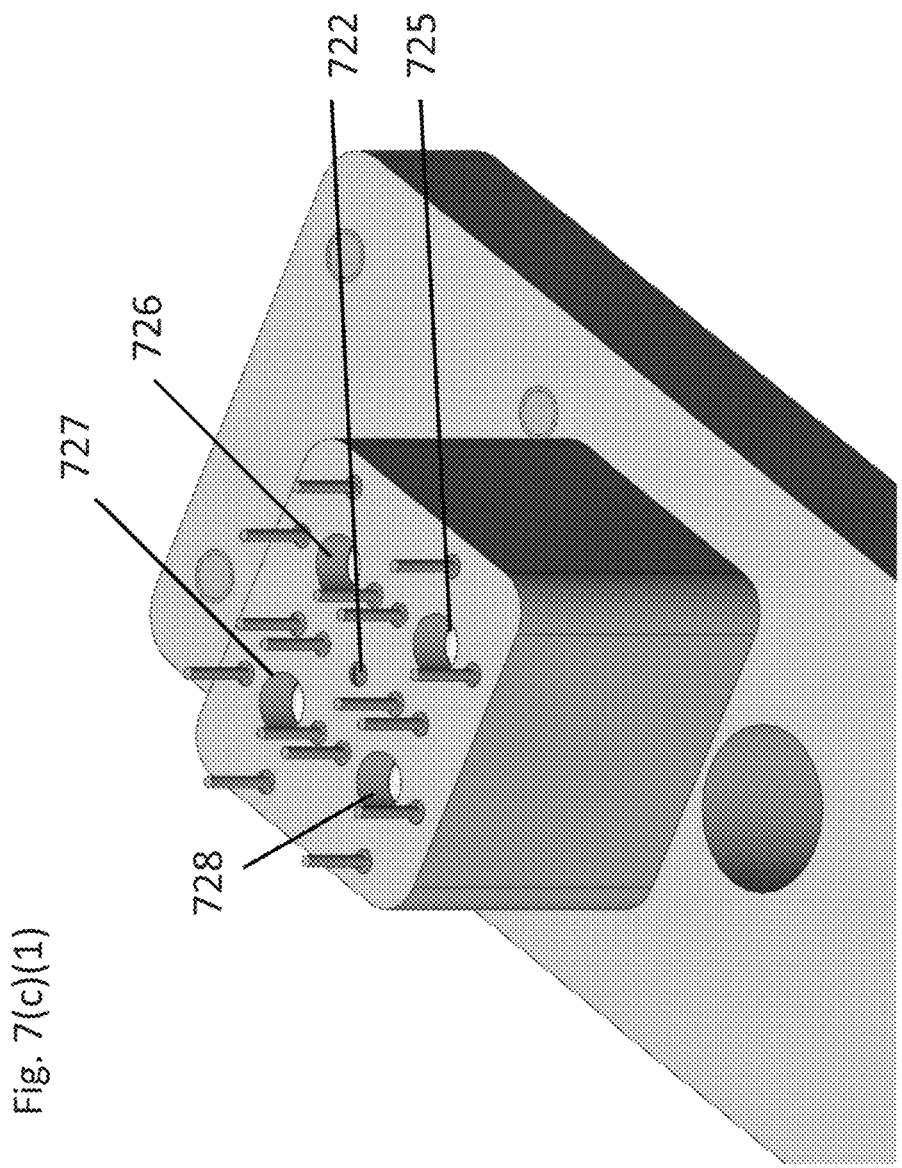
Fig. 7(c)(1)

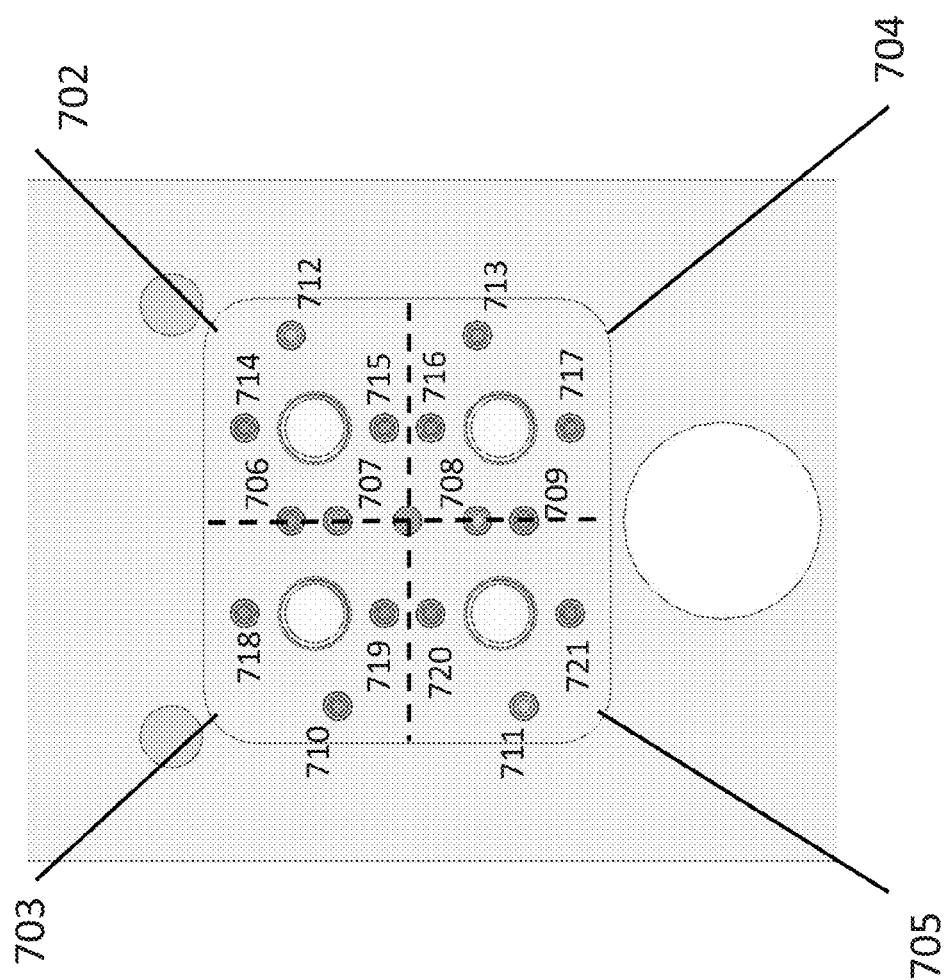
Fig. 7(c)(2)

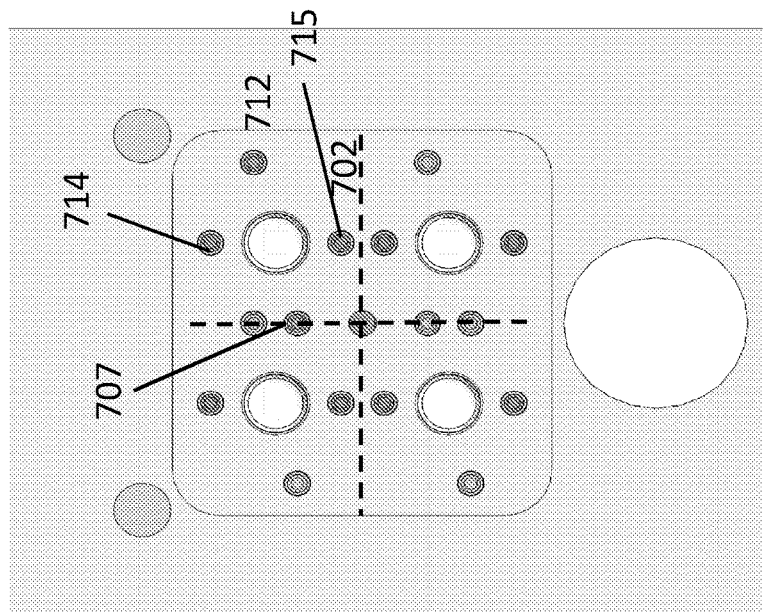
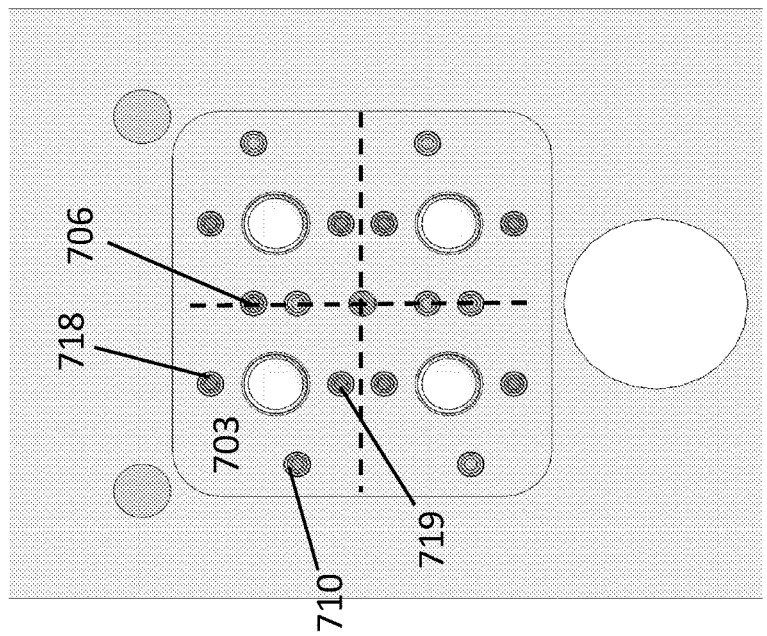
Fig. 7(d)-(e)

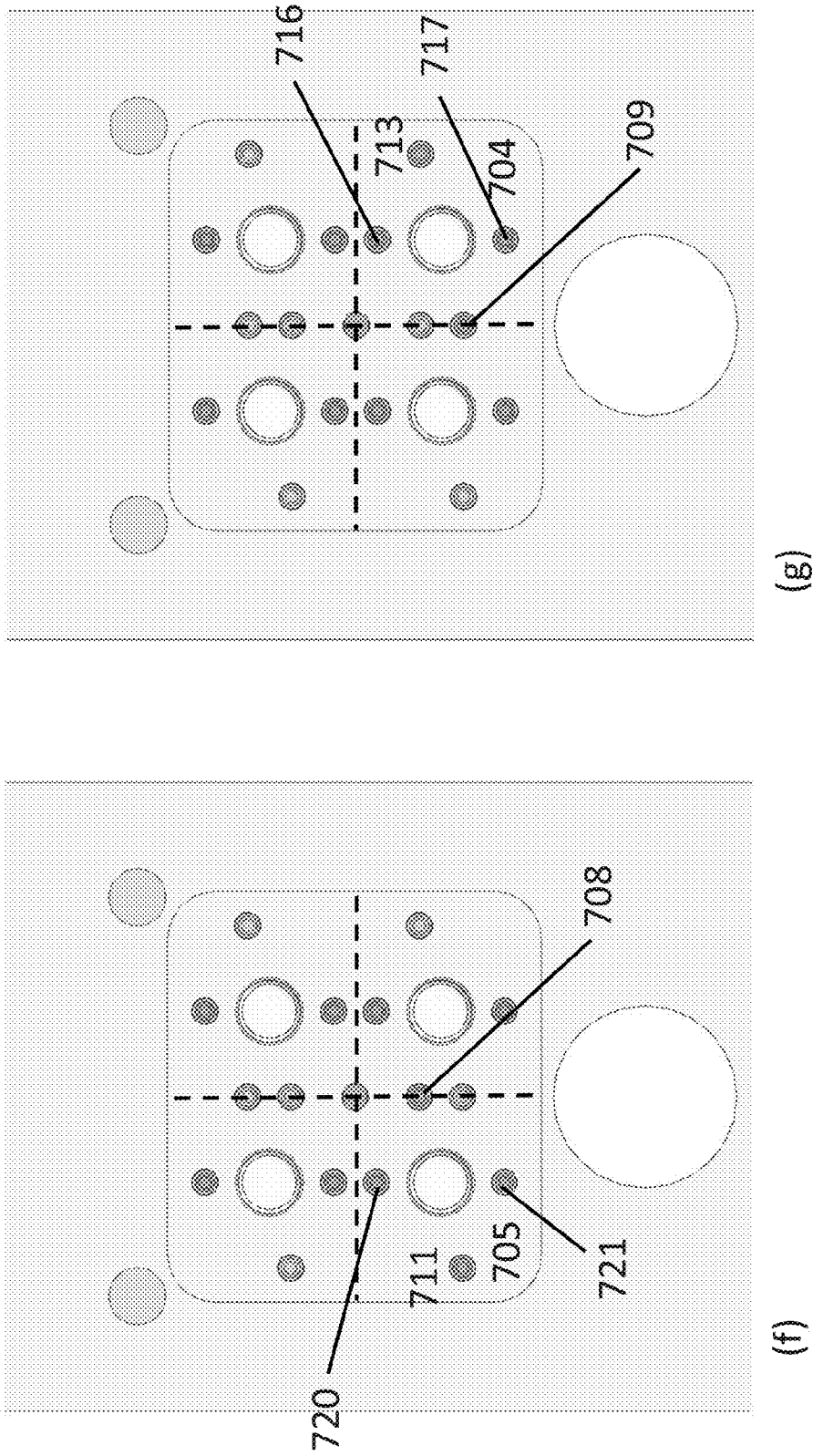
Fig. 7(f)-(g)

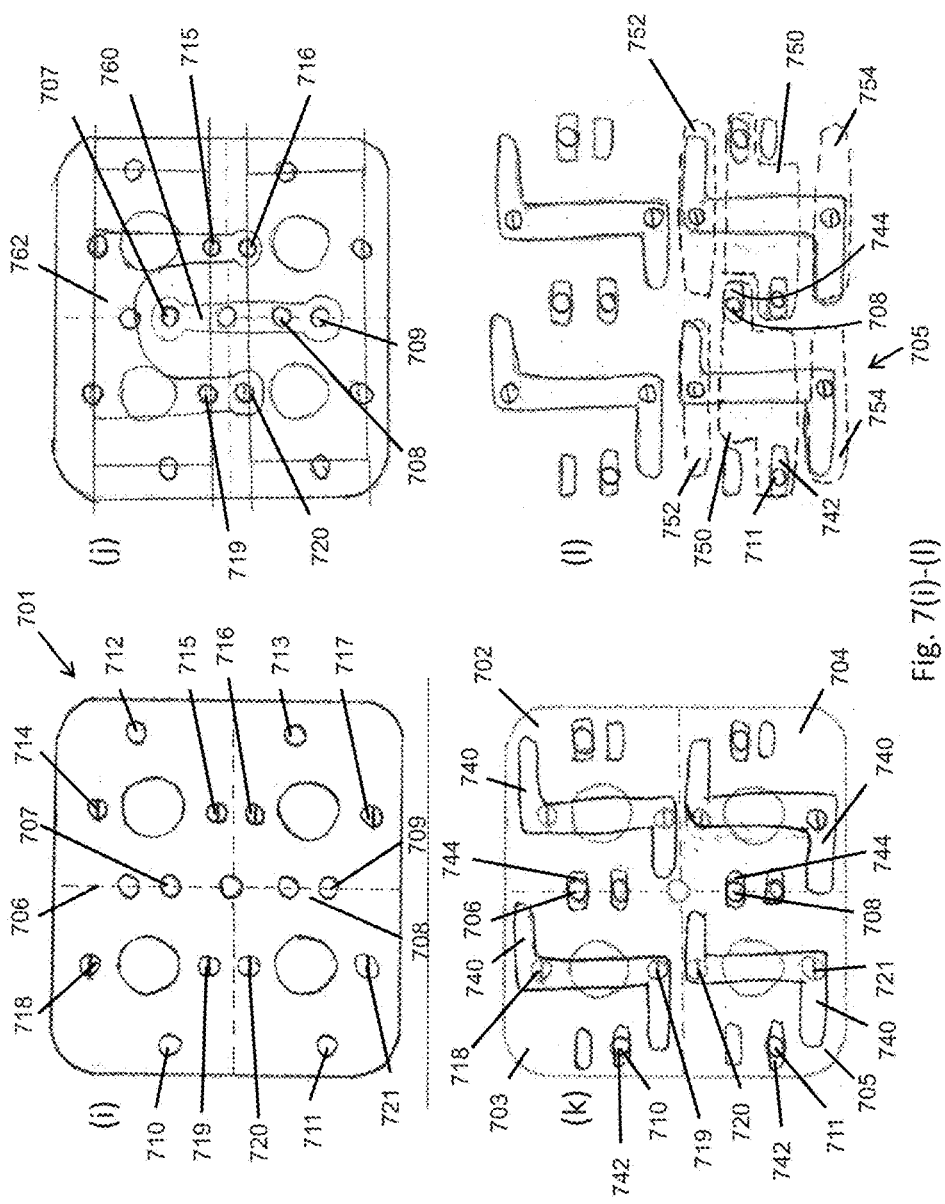
Fig. 7(i)-(l)

ASSAY APPARATUSES, METHODS AND REAGENTS

CROSS REFERENCE TO RELATED APPLICATIONS

The present patent application claims priority under 35 U.S.C. § 119 (e) to U.S. provisional application No. 61/749,097 entitled "Assay Apparatus, Methods and Reagents" filed on 4 Jan. 2013. The disclosure of this parent application is incorporated by reference in its entirety. Reference is also made to U.S. Application Publication Nos. 2011/0143947, 2012/0195800, 2007/0231217, 2009/0263904, and 2011/025663. The disclosures of each of these applications are incorporated herein by reference in their entireties.

FIELD OF THE INVENTION

The invention relates to apparatuses, systems, methods, reagents, and kits for conducting assays. Certain embodiments of the apparatuses, systems, methods, reagents, and kits of the invention may be used for conducting automated sampling, sample preparation, and/or sample analysis in a multi-well plate assay format.

BACKGROUND OF THE INVENTION

Numerous methods and systems have been developed for conducting chemical, biochemical, and/or biological assays. These methods and systems are essential in a variety of applications including medical diagnostics, food and beverage testing, environmental monitoring, manufacturing quality control, drug discovery, and basic scientific research.

Multi-well assay plates (also known as microtiter plates or microplates) have become a standard format for processing and analysis of multiple samples. Multi-well assay plates can take a variety of forms, sizes, and shapes. For convenience, some standards have appeared for instrumentation used to process samples for high-throughput assays. Multi-well assay plates typically are made in standard sizes and shapes, and have standard arrangements of wells. Arrangements of wells include those found in 96-well plates (12×8 array of wells), 384-well plates (24×16 array of wells), and 1536-well plates (48×32 array of wells). The Society for Biomolecular Screening has published recommended microplate specifications for a variety of plate formats (see http://www.sbsonline.org).

A variety of plate readers are available for conducting assay measurements in multi-well plates including readers that measure changes in optical absorbance, emission of luminescence (e.g., fluorescence, phosphorescence, chemiluminescence, and electrochemiluminescence), emission of radiation, changes in light scattering, and changes in a magnetic field. U.S. Patent Application Publication 2004/0022677 and U.S. Pat. No. 7,842,246, respectively, of Wohlstadter et al. describe solutions that are useful for carrying out singleplex and multiplex ECL assays in a multi-well plate format. They include plates that comprise a plate top with through-holes that form the walls of the wells and a plate bottom that is sealed against the plate top to form the bottom of the wells. The plate bottom has patterned conductive layers that provide the wells with electrode surfaces that act as both solid phase supports for binding reactions as well as electrodes for inducing electrochemiluminescence (ECL). The conductive layers may also include electrical contacts for applying electrical energy to the electrode surfaces.

Despite such known methods and systems for conducting assays, improved apparatuses, systems, methods, reagents, and kits for conducting automated sampling, sample preparation, and/or sample analysis in a multi-well plate assay format are needed.

SUMMARY OF THE INVENTION

Accordingly, the invention provides a method for focusing an optical sensor to a spaced apart platform comprising the steps of: (a) providing at least a higher, middle and lower patterned surface, wherein the middle patterned surface and the platfoint are aligned to each other and wherein a first distance between the higher and middle patterned surfaces and a second distance between the middle surface and lower patterned surface are substantially equal; (b) obtaining a first difference in contrast values between the higher and middle patterned surfaces with the optical sensor; (c) obtaining a second difference in contrast values between the middle and lower patterned surfaces with the optical sensor; and (d) comparing the first and second differences in contrast values.

The invention further provides a focusing mechanism for an optical sensor comprising at least a higher, middle and lower patterned surface spaced apart from the optical sensor; wherein the middle patterned surface is aligned to a target surface to be focused by the optical sensor and the middle patterned surface, wherein a first distance between the higher and middle patterned surfaces and a second distance between the middle surface and lower patterned surface are substantially equal, wherein the optical sensor and the patterned surfaces are moved relative to each other until a difference between a first and a second differences in contrast values between the higher and middle patterned surfaces and between the middle and lower patterned surfaces is less than a predetermined value; and wherein an illuminating source is positioned to project light through the higher, middle and lowered patterned surfaces toward the optical sensor.

The invention contemplates an instrument comprising: (a) a contact platform, wherein the contact platform comprises a plurality of interrogation zones and each interrogation zone comprises at least a pair of electrical contacts to apply a voltage potential to the interrogation zone, (b) a controller operatively connected to a voltage source, wherein the voltage source is connectable to one or more pairs of electrical contacts, and (c) a multiplexer connected to the controller and to the voltage source for selectively connecting the voltage source to the pair of electrical contacts of a single interrogation zone or connecting the voltage source to the pairs of electrical contacts of more than one interrogation zones.

The instrument of the invention also includes: (a) a contact platform, wherein the platform comprises a plurality of interrogation zones and each interrogation zone comprises at least a pair of electrical contacts to conduct a voltage potential to the interrogation zone, (b) a controller operatively connected to a voltage source, wherein the voltage source is connectable to one or more pairs of electrical contacts, and (c) a means connected to the controller and the voltage source for switching from a first connection between the voltage source and the electrical contacts of a single interrogation zone to a second connection between the voltage source and the electrical contacts of one or more interrogation zones.

The instrument is preferably adapted to interrogate samples contained in a multi-well plate, and comprises: (a) a carriage frame configured to support the multi-well plate and the carriage frame is movable relative to a contact platform, wherein the multi-well plate comprises a plurality of wells, wherein the wells are arranged in a M×N matrix, and wherein the contact platform comprises a plurality of interrogation zones, wherein each interrogation zone comprises at least a pair of electrical contacts to conduct a voltage potential to at least one well; (b) a controller operatively connected to a motor to move the carriage frame relative to the contact platform and operatively connected to a voltage source, wherein the voltage source is connectable to one or more pairs of electrical contacts; and (c) a multiplexer connected to the controller and to the voltage source for selectively connecting the voltage source to the pair of electrical contacts of a single interrogation zone or connecting the voltage source to at least one pair of electrical contacts of more than one interrogation zones.

Another embodiment of the invention is a method for interrogating samples contained in a multi-well plate having a M×N matrix of wells comprising the steps of (a) providing a contact platform having a plurality of interrogation zones, (b) providing at least a pair of electrical contacts for each interrogation zone, wherein each interrogation zone is adapted to interrogate a single well, (c) selectively applying a voltage potential to: (i) one interrogation zone to interrogate one or more wells simultaneously or (ii) a plurality of interrogation zones to interrogate a plurality of wells, and (d) moving the multi-well plate relative to the platform to interrogate additional wells.

In a specific embodiment, the invention includes an instrument for conducting luminescence assays in a multi-well plate. The instrument comprises a light detection subsystem and a plate handling subsystem, wherein the plate handling subsystem comprises:

(a) a light-tight enclosure comprising a housing and a removable drawer, wherein
  (x) the housing comprises a housing top, a housing front, one or more plate introduction apertures, a detection aperture, a sliding light-tight door for sealing the plate introduction apertures, and a plurality of alignment features, wherein the housing is adapted to receive the removable drawer, and
  (y) the removable drawer comprises:
    (i) an x-y subframe including plurality of companion alignment features configured to mate and engage with the plurality of alignment features to align the removable drawer within the housing relative to the light detection subsystem, wherein a weight of the removable drawer is supported by the housing top;
    (ii) one or more plate elevators with a plate lifting platform that can be raised and lowered, wherein the one or more plate elevators are positioned below the plate introduction apertures;
    (iii) a plate translation stage for translating a plate in one or more horizontal directions, wherein the stage comprises a plate carriage for supporting the plate, the plate carriage has an opening to allow the plate elevators positioned below the plate carriage to access and lift the plate, and the plate translation stage is configured to position plates below the detection aperture and to position the plates above the plate elevators; and (b) one or more plate stackers mounted on the housing top, above the plate introduction apertures, wherein the plate stackers are configured to receive or deliver plates to the plate elevators; and wherein the light detection subsystem comprises a light detector mounted on the enclosure top and coupled to the detection aperture with a light-tight seal.

The instrument can be used to conduct luminescence assays in a multi-well plate, and comprises a plate handling subsystem including a plate carriage for supporting the multi-well plate, wherein the plate carriage comprises a frame and a plate latching mechanism. The plate latching mechanism comprises:

(a) a plate carriage ledge;
(b) a plate clamp arm perpendicular to the ledge and comprising a proximate and a distal end relative to the ledge, wherein the arm is attached to the frame at the proximate end and the arm is rotatable in an x-y plane at the distal end, and the arm further comprises an upper clamp including an angled surface configured to engage with the plate;
(c) a plate positioning element comprising a rod, a pedal and a spring, wherein the rod is substantially perpendicular to the arm, substantially parallel to the ledge, and attached to the distal end of the arm via the spring, and the pedal is attached to the rod at an angle; and
(d) a plate wall substantially parallel to the arm and substantially perpendicular to and disposed between the positioning element and the ledge, the wall comprising (i) a lower plate clamp configured to engage with a multi-well plate skirt, and (ii) a lower plate clamp ramp configured to drive the lower plate clamp toward the skirt.

The present invention is further directed to a method of engaging a multi-well plate in the instrument immediately discussed above. The method comprises the following steps:

(a) placing the plate on the frame;
(b) compressing the spring of the plate positioning element, thereby pushing the pedal against the plate toward the ledge and rotating the arm in the x-y plane toward the plate;
(c) contacting the upper clamp with the plate, thereby pushing the plate toward the carriage wall;
(d) contacting the lower plate clamp with the skirt, thereby locking the plate within the carriage.

Moreover, the invention provides an instrument for conducting luminescence assays in a multi-well plate, and comprises a plate handling subsystem including a plate carriage for supporting the multi-well plate, and a plate latching mechanism, wherein the multi-well plate has at least a first, second, third and fourth side and wherein the first and third sides are substantially parallel to each other and the second and fourth sides are substantially parallel to each other, wherein the plate carriage defines an aperture having a shape substantially the same as the multi-well plate and having dimensions smaller than the multi-well plate to support a ledge positioned around a perimeter of the multi-well plate, wherein the plate carriage further comprises a first (501) and second (513) stop corresponding to the first and second sides of the multi-well plate, respectively.

wherein the plate latching mechanism is movable from an open configuration to accept one multi-well plate to a clamping configuration to latch the multi-well plate to the plate carriage, wherein the plate latching mechanism comprises a first latching member (509) biased to the clamping position and having a pedal (511) adapted to push the first side of the multi-well plate toward the first stop and a plate clamp arm (502) biased to the clamping position and having a bracket (503) pivotally connected to the plate clamp arm (502) and is adapted to push the second side toward the second stop (513), wherein the first latching mechanism (509) is connected to the plate clamp arm (502), and wherein the plate latching mechanism comprises at least one biased clamp (515) positioned proximate to second stop (513) to clamp to the skirt of the multi-well tray to the plate carriage.

Still further, the invention provides a system comprising
(i) a multi-well assay plate selected from the group consisting of a single-well addressable plate or a multi-well addressable plate; and
(ii) an apparatus configured to measure electrochemiluminescence (ECL) from a single well of the single-well addressable plate and from a grouping of wells of the multi-well addressable plate.

The present invention further includes an apparatus for measuring luminescence from a multi-well plate of a plate type selected from the group consisting of a single well addressable plate or a multi-well addressable plate, the apparatus comprising:
(i) a plate type identification interface for identifying the plate type;
(ii) a plate translation stage for holding and translating the multi-well plate in the x-y plane;
(iii) a plate contact mechanism comprising a plurality of contact probes and positioned below the plate translation stage and within the range of motion of the stage, wherein the mechanism is mounted on a contact mechanism elevator that can raise and lower the mechanism to bring the probes into and out of contact with a bottom contact surface the plate when positioned on the translation stage;
(iv) a voltage source for applying potential through the contact probes to the plate; and
(v) an imaging system positioned above the plate translation stage and in vertical alignment with the plate contact mechanism, wherein
(a) the imaging system is configured to image a P×Q matrix of wells, the plate contact mechanism is configured to contact the bottom contact surface associated with the matrix and the plate translation stage is configured to translate a plate to position the matrix in alignment with the imaging system and plate contact mechanism;
(b) the apparatus is configured to sequentially apply a voltage to each well in the matrix of a single well addressable plate and image the matrix; and
(c) the apparatus is configured to simultaneously apply a voltage to each well in the matrix of a multi-well addressable plate and image the matrix.

Also provided is a method for measuring luminescence from a single-well addressable plate or a multi-well addressable plate, wherein the method comprises:
(a) loading a plate on the plate translation stage;
(b) identifying the plate as being a single well or multi-well addressable plate;
(c) moving the plate translation stage to align a first P×Q matrix of wells with the plate contact mechanism and imaging system;
(d) raising the plate contact mechanism so that the contact probes on the contact mechanism contact the bottom contact surface associated with the P×Q matrix of wells;
(e) generating and imaging luminescence in the P×Q matrix by sequentially applying voltage to each well in the group while the group is imaged, if the plate is a single well addressable plate;
(f) generating and imaging luminescence in the P×Q matrix by simultaneously applying voltage to each well in the matrix while the matrix is imaged, if the plate is a multi-well addressable plate; and
(g) repeating steps (c) through (f) for additional P×Q matrices in the plate.

BRIEF DESCRIPTION OF DRAWINGS

FIGS. 1(*a*)-(*b*) show a front and rear view, respectively, of apparatus 100 with a stylized cover and FIGS. 1(*c*)-(*d*) show the corresponding front and rear views, respectively, of the apparatus without the cover.

FIG. 3 shows a view of the removable drawer of the plate handling subsystem within apparatus 100.

FIGS. 4(*a*)-(*f*) show various detailed views of the removable drawer 240 and the subcomponents positioned within the drawer.

FIGS. 6(*a*)-(*b*) show two alternative embodiments of an optical focusing mechanism that can be incorporated into the apparatus.

DESCRIPTION OF SPECIFIC EMBODIMENTS OF THE INVENTION

Figure 2A:
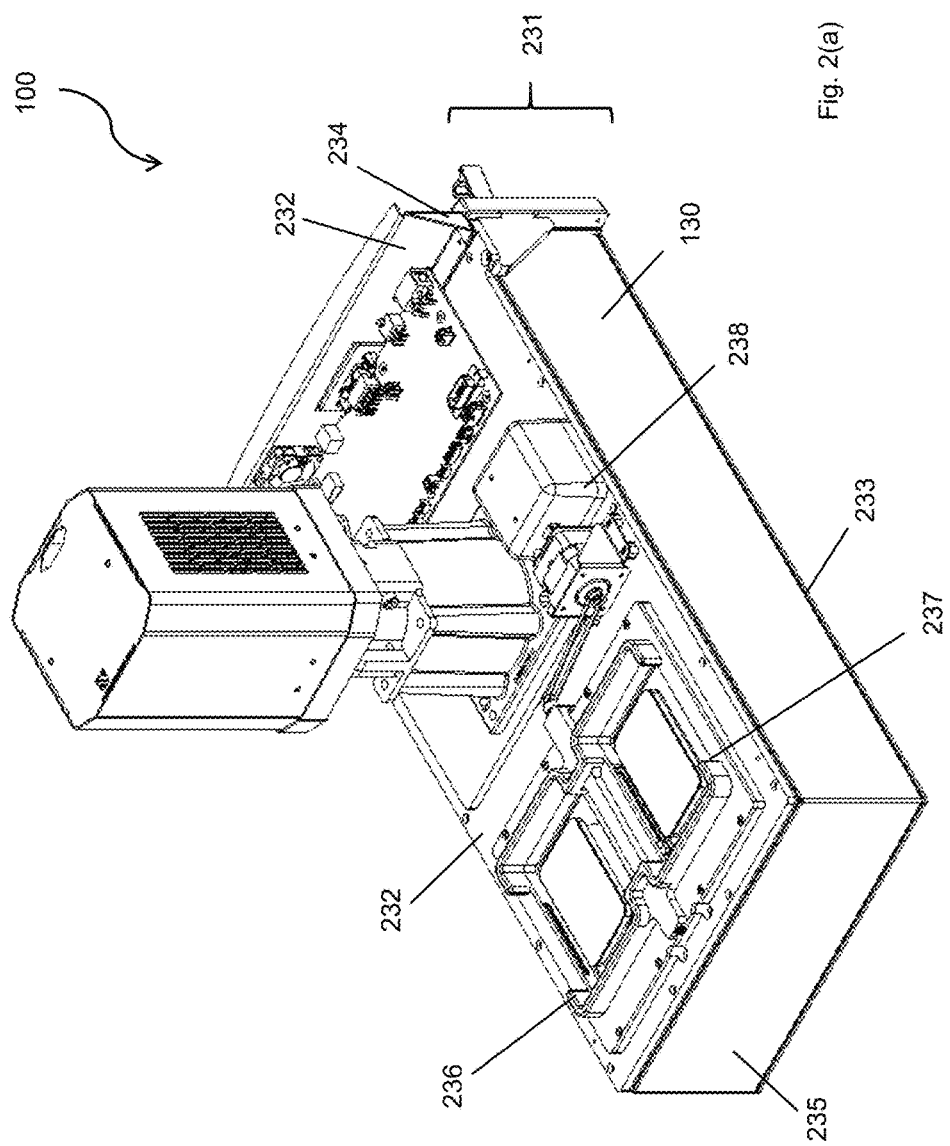
FIGS. 2(*a*)-(*c*) show detailed views of the plate handling subsystem and light detection subsystem.

The Detailed Description section provides descriptions of certain embodiments of the invention that should not be considered limiting but are intended to illustrate certain inventive aspects. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element. Furthermore, a claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than ancillary elements or inconsequential activities which are ordinarily associated with the invention) instead of the "comprising" term. Any of these three transitions can be used to claim the invention.

Described herein is an apparatus for conducting assays in a multi-well plate format that have one or more of the following desirable attributes: (i) high sensitivity, (ii) large dynamic range, (iii) small size and weight, (iv) array-based multiplexing capability, (v) automated operation; and (vi) ability to handle multiple plates. We also describe components and subsystems used in such an apparatus and methods of using the apparatus and subsystems. The apparatus and methods may be used with a variety of assay detection techniques including, but not limited to, techniques measuring one or more detectable signals. Some of them are suitable for electrochemiluminescence measurements and, in particular, embodiments that are suitable for use with multi-well plates with integrated electrodes (and assay methods using these plates) such as those described in U.S. Publication 2004/0022677 and U.S. Pat. No. 7,842,246, respectively, of Wohlstadter et al., and U.S. application Ser. No. 11/642,970 of Glezer et al.

In a preferred embodiment, an apparatus is provided for conducting luminescence assays in multi-well plates. One embodiment comprises a light detection subsystem and a plate handling subsystem, wherein the plate handling subsystem includes a light-tight enclosure that provides a light-free environment in which luminescence measurements can be carried out. The enclosure includes a housing and a removable drawer that is placed within the housing. The housing also includes a housing top having one or more plate introduction apertures through which plates can be lowered onto or removed from a plate translation stage (manually or mechanically) within the drawer. A sliding light-tight door in the housing is used to seal the plate introduction apertures from environmental light prior to carrying out luminescence measurements. The housing further includes a detection aperture that is coupled to a light detector mounted on the housing top and one or more plate stackers mounted on the housing top above the plate introduction apertures, wherein the plate stackers are configured to receive or deliver plates to plate elevators within the removable drawer. The removable drawer includes a plate translation stage for translating a plate horizontally in the drawer to zones within the apparatus where specific assay processing and/or detection steps are carried out. The removable drawer also includes one or more plate elevators with a plate lifting platform that can be raised and lowered within the drawer, wherein the plate elevators are positioned below the one or more plate introduction apertures. The plate translation stage is configured to position plates below the detection aperture and to position plates above the plate elevators on the plate lifting platforms.

The apparatus also includes a light detector which is mounted to the detection aperture on the housing top (e.g., via a light-tight connector or baffle). In certain embodiments, the light detector is an imaging light detector such as a CCD camera and may also include a lens. The light detector may be a conventional light detector such as a photodiode, avalanche photodiode, photomultiplier tube, or the like. Suitable light detectors also include arrays of such light detectors. Light detectors that may be used also include imaging systems such as CCD and CMOS cameras. The light detectors may also include lens, light guides, etc. for directing, focusing and/or imaging light on the detectors. In certain specific embodiments, an imaging system is used to image luminescence from arrays of binding domains in one or more wells of an assay plate and the assay apparatus reports luminescence values for luminescence emitted from individual elements of the arrays. The light detector is mounted on the housing top with a light-tight seal. Additional components of the apparatus include plate contacts for making electrical contact to the plates and providing electrical energy to electrodes in wells positioned under the light detector (e.g., for inducing ECL).

Specific embodiments of the apparatus of the invention are illustrated in the Figures. FIGS. 1(a)-(b) show a front and rear view, respectively, of apparatus 100 with a stylized cover, and FIGS. 1(c)-(d) show the corresponding front and rear views, respectively, of the apparatus without the cover. As shown, e.g., in FIG. 1(c), the apparatus includes a light detection subsystem 110 and a plate handling subsystem 120. A more detailed view is provided in FIGS. 2(a)-(b). The plate handling subsystem 120 includes a light tight enclosure 130 comprising a housing 231 having a housing top 232, bottom 233, front 234, and rear 235. The housing also includes a plurality of alignment features and the housing is adapted to receive a removable drawer 240 comprising a removable drawer front and consisting of a unitary casting element. The walls of the removable drawer define a rigid x-y subframe, 415 in FIG. 4(d), including a plurality of companion alignment features. When the drawer is properly placed within the housing, the alignment and companion alignment features mate and engage, thereby aligning the drawer and its components with the components of the light detection subsystem. When the alignment/companion alignment features are engaged, the weight of the removable drawer is supported by the housing top. The removable drawer 240 in the apparatus 100 depicted in FIGS. 1(a)-(b) is best shown in FIG. 3, being in the partially opened or closed position. Removable drawer 240 is also illustrated in FIG. 4(a) carrying various internal subsystems described in detail below and in FIG. 4(b) being installed within housing 231, where housing rear 235 and a housing side are omitted for clarity. FIG. 4(c) shows housing 231 with an opening and alignment features 405, 406, and 407 positioned and dimensioned to receive removable drawer 240.

In one embodiment, the plate handling subsystem further comprises a plate sensor configured to detect a plate in the subsystem. Suitable plate sensors include, but are not limited to a capacitive sensor, contact switch, ultrasonic sensor, weight sensor, or an optical sensor, or a combination thereof.

Figure 2C:
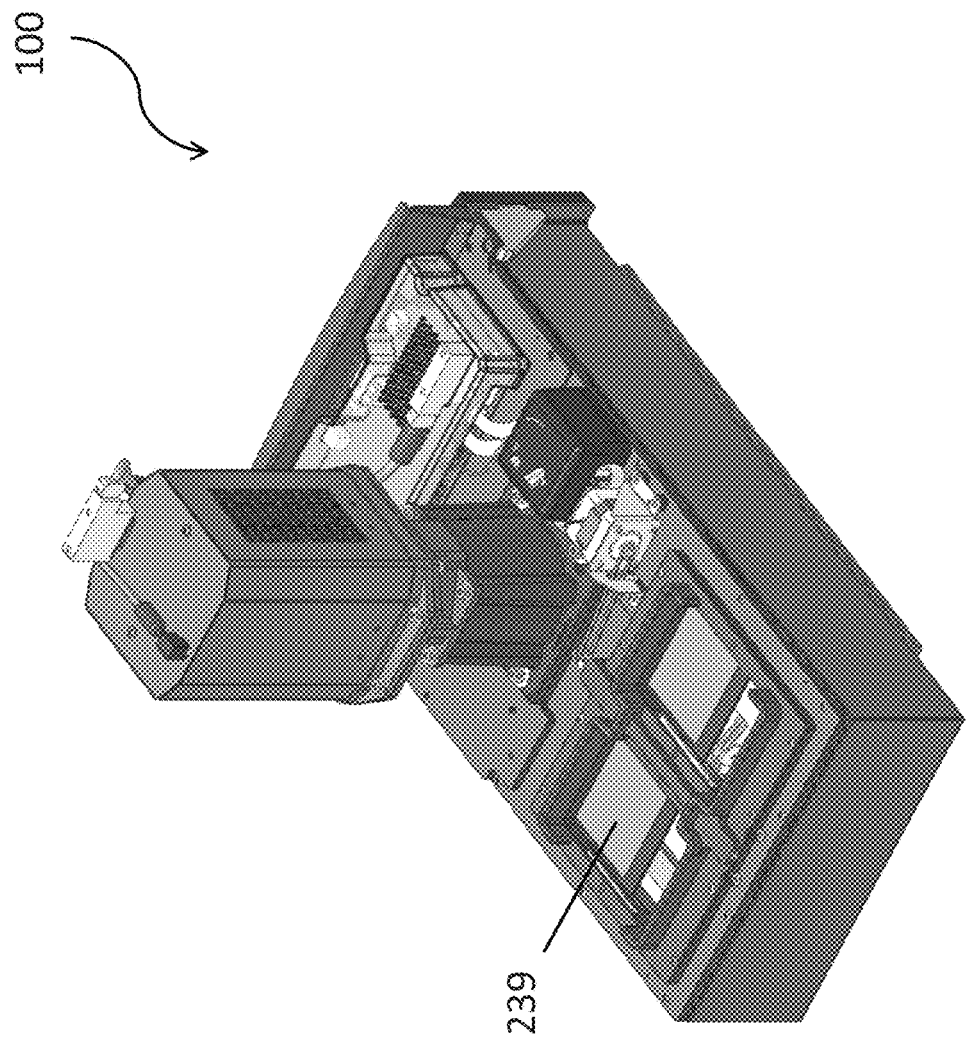

Referring to FIG. 2(a), the housing top 232 also includes one or more plate introduction (and ejection) apertures, 236 and 237, respectively, through which plates are lowered onto or removed from the plate translation stage (manually or mechanically). A sliding light-tight door (shown in FIG. 2(c) as 239) is used to seal the plate introduction apertures 236, 237 from environmental light prior to carrying out luminescence measurements. Moreover, the housing top also includes an identifier controller to read and process data stored to an identifier on the plates. In one embodiment, the identifier controller is a bar code reader (238) mounted via a light-tight seal over an aperture in the housing top, where the bar code reader is configured to read bar codes on plates placed on the plate translation stage within the housing. In a preferred embodiment, the bar code on a plate is read once the plate has been lowered into the drawer. In an alternative or additional embodiment, the plates comprise an EEPROM or an RFID and the housing top and/or drawer includes an identifier controller suitable for communicating with each of these identifiers. In a further additional embodiment, an identifier controller can be provided separately from the apparatus. In this embodiment, information stored to an identifier attached to a plate or associated with a plate or a set of plates is transferred to the apparatus via a computer and/or network attached thereto and/or manually input via a user interface of the computer and/or network. In this regard, reference is made to U.S. application Ser. Nos. 12/844,345 and 13/191,000, the disclosures of which are incorporated herein by reference.

The plate handling subsystem further includes one or more plate stackers mounted on the housing top 232 above the plate introduction apertures 236, 237, wherein the plate stackers are configured to receive or deliver plates to the plate elevators. The plate handling subsystem optionally includes a heating and/or cooling mechanism (e.g., a resistance heater, a fan, heat sinks, or a thermoelectric heater/cooler) to maintain temperature of the subsystem under desired conditions. It may also include a humidity control mechanism (e.g., a humidifier and/or dehumidifier, or a desiccant chamber to maintain the humidity of the subsystem under desired conditions.

A detailed view of the removable drawer of the plate handling subsystem is shown in FIG. 4. Referring to FIG. 4(a), the drawer includes (i) a plate elevator mechanism 400 with plate lifting platforms, 401 and 402, that can be raised and lowered; and (ii) a plate translation stage 403 for translating a plate in one or more horizontal directions, wherein the stage includes a plate carriage 404 for supporting the plate. The plate carriage 404 preferably has an opening 420 to allow the plate elevators 400 positioned below the plate carriage 404 to access and lift a plate, and the plate translation stage 403 is configured to position plates below the detection aperture on housing top 232 and below the light detectors within the light detection system 110, and to position the plates above the plate elevators 400. The plate lifting platforms 401, 402 of the plate elevator 400 preferably comprises a non-skid surface to prevent shifting of the plate on the plate lifting platform during movement in the apparatus. The plate translation stage 403 has horizontal motions, e.g., motions on a substantially horizontal plane or in an X-direction and Y-direction for translating a plate horizontally in the drawer to one or more regions within the apparatus where specific assay processing and/or detection steps are carried out. In one non-limiting example, as illustrated in FIG. 4(e), plate translation stage 403 is movable in one horizontal direction along rail 422, and plate carriage 404 is movable on rail 424 on plate translation stage 403 in an orthogonal horizontal direction. In a preferred embodiment, the plate translation stage has two axes of motion, x and y, and motors coupled to the axes of motion allow for automated movement of plates on the stage.

The inclusion of a removable drawer 240 in the light-tight enclosure 130 enhances the serviceability and manufacturability of the apparatus. In order to ensure proper alignment of the drawer 240 within the housing 231 and therefore, proper alignment of the subsystems within the drawer 240 with the light detection subsystem 110, the housing includes a plurality of alignment features and the x-y subframe of the drawer includes a plurality of companion alignment features configured to mate and engage with the alignment features of the housing. A cut-away view of the drawer 240 placed within the housing 231 with housing rear 235 and a housing side omitted for clarity and properly aligned with the light detection subsystem 110 is shown in FIG. 4(b).

In a preferred embodiment, the alignment features of drawer 240 comprise a plurality of holes and the corresponding alignment features on housing 231 comprise a plurality of pins sized to fit within the holes. As shown in FIG. 4(c), the housing 231 preferably includes at least three alignment pins, pins 405 and 406 being positioned on the housing front 234, and pin 407, which is positioned on the opposite end of the housing. Additional alignment features can be included in the housing and drawer, as necessary. Preferably, the alignment features are positioned or calibrated relative to the housing top, such that the weight of the drawer 240 is supported by the housing top 232. The companion alignment features on the drawer that are configured to mate and engage with alignment pins 405, 406, and 407, are shown in FIG. 4(d) as holes 408, 409, 410 (in the embodiment shown in FIG. 4(d), alignment pin 405 mates and engages with hole 408, pin 406 mates and engages with hole 409, and pin 407 mates and engages with hole 410). In addition, the drawer also includes alignment latches, 416 and 417 (shown in FIG. 4(a)) that mate and engage with companion alignment catches, 418 and 419 (FIG. 4(c)), to lock/unlock the drawer within the housing.

Due to the alignment features 405-407 and 408-410 being positioned or calibrated to housing top 232, while removable drawer 240 is inserted into housing 231 guided by X-Y frame 415, after removable drawer 240 is fully inserted into housing 231, the weight of drawer 240 and components thereon are supported by housing top 232. An advantage of this feature is that since light detection system 110 is also mounted on housing top 232 any calibration or alignment of the subsystems on drawer 240 to light detection system 110 can be carried out directly relative to the light detection system 110, without having to taking into account any gap or spacing between drawer 240 and housing top 232.

One or more additional engagement/locking features can be included in the housing and/or drawer, for example, as shown in FIG. 4(e), in which spring loaded pin 411 is mounted to the drawer 240 and configured to mate and engage with a hole 412 positioned in the plate carriage 403. In one embodiment, a solenoid is used to actuate a spring loaded pin, such as pin 411. In the embodiment shown in FIG. 4(f), when the plate carriage and plate translation stage are aligned, the alignment feature in the plate translation stage, pin 411, mates and engages with a corresponding locking feature in the plate carriage, element 412, as shown in FIG. 4(f). These alignment and/or engagement features lock the plate carriage in place to protect the subassembly from damage, e.g., during shipping and/or installation.

In a further preferred embodiment, as shown in FIGS. 4(c)-(d), the housing top comprises an electrical connection contact mechanism 413, and the drawer front comprises a companion electrical connection, element 414, wherein the electrical connection and its companion are configured to mate and engage with one another upon proper insertion and alignment of the drawer within the housing.

Figure 5A:
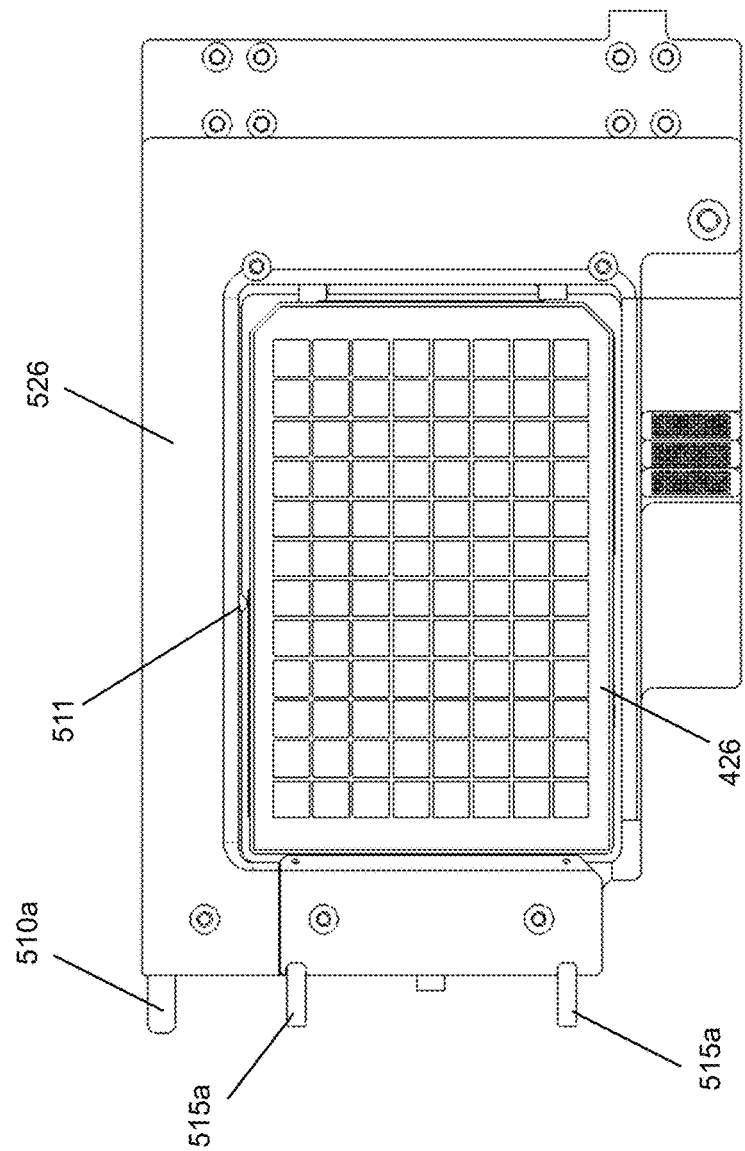
FIGS. 5(*a*)-(*o*) show detailed views of the plate carriage and plate latching mechanism.
Figure 5B:
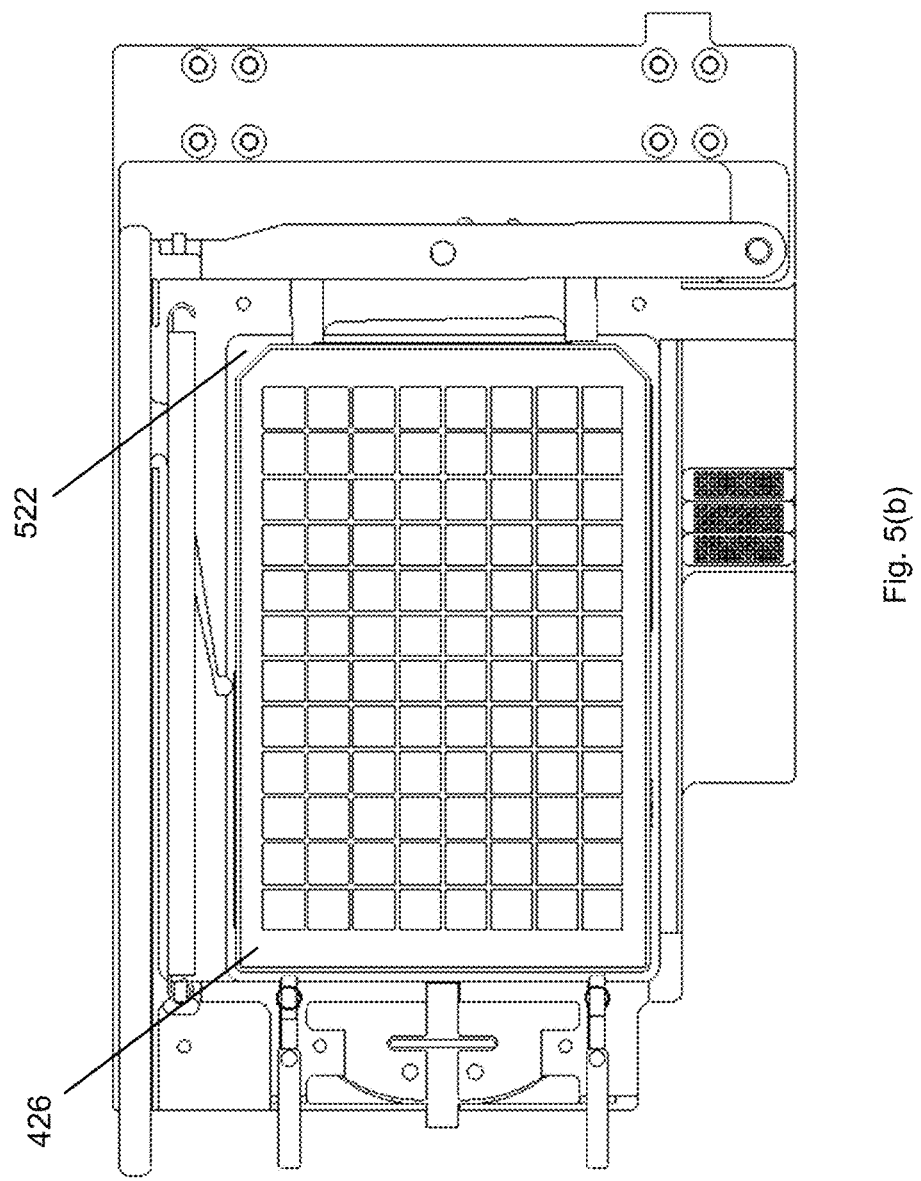

Referring to FIG. 4(a), in a preferred embodiment, the plate carriage comprises a carriage platform 404 and a plate latching mechanism configured to receive and engage an exemplary plate hereinafter labeled as 426 placed on the carriage platform 404, as shown in FIG. 5(a)-(b) (FIG. 5(a) shows a view of the plate carriage with a plate 426 locked in place and FIG. 5(b) shows the same view with the components of the plate latching mechanism visible and engaged with the plate in a locked position). As shown in FIG. 5(b), the outside edges of the plate follow a standard design convention for multi-well plates and include a skirt 522 that surrounds and is at a height lower than the walls of the plate (an enlarged view is shown in FIG. 5(o)). In other words, skirt 522 is positioned proximate the bottom of plate 426. The plate latching mechanism is designed to push the outside edge of the skirt on two orthogonal sides of the plate against two corresponding physical stops in the plate carriage, to provide a defined and reproducible positioning of the plate in the carriage. The plate latching mechanism is also designed to apply a downward physical force in defined locations on the top of the plate skirt to reproducibly and fixedly hold the plate in the vertical dimension.

A view of the plate carriage 404 and plate latching mechanism with a plate 420 is shown in FIG. 5(a)-(b). A sequence illustrating the operations of the plate latching mechanism is shown in FIGS. 5(c)-5(f) and discussed below. In a specific embodiment, the plate carriage 404 supports a multi-well plate 426 (or a consumable having the same footprint and external physical geometry as a multi-well/microtitre plate configured for use in an apparatus as described herein) having at least a first, second, third and fourth side and wherein the first and third sides are substantially parallel to each other and the second and fourth sides are substantially parallel to each other. The plate carriage 404 defines an aperture 420 having a shape substantially the same as the multi-well plate 426 and having dimensions smaller than the multi-well plate to support a skirt or ledge 522 positioned around a perimeter of the multi-well plate 426. The plate carriage further comprises a first (501) and second (513) stop surface that when the plate 426 is fully latched, define the horizontal positions of the skirt 522 on first and second sides of the multi-well plate, respectively. The plate latching mechanism is movable from an open configuration, as best shown in FIGS. 5(i) and 5(j) to accept a plate 426 to a clamping configuration to latch the plate to the plate carriage, as best shown in FIGS. 5(a) and 5(b).

The plate latching mechanism comprises (i) a first latching member (509) biased to the clamping position and consisting of a pedal 511, an actuating rod 510, and a spring 512, which provides the biasing force and preferably has a high spring force. The pedal (511) is adapted to push the first side of the multi-well plate 426 toward the first stop 501 and a plate clamp arm (502) also biased to the clamping position by spring 512, wherein the first latching mechanism (509) is connected to the plate clamp arm (502). The plate latching mechanism further includes (ii) a bracket (503) pivotally connected to the plate clamp arm (502) and adapted to push the second side of plate 426 toward the second stop (513). The plate latching mechanism also comprises (iii) at least one biased clamp (515) positioned proximate to second stop (513) to clamp to the skirt 522 of the multi-well plate 426 to the plate carriage 404, thereby preventing vertical motion. Clamp 515 engages with the plate skirt and applies a downward force on the skirt of the plate. The bracket (503) preferably comprises at least two legs (504, 506) and both are in contact with the fourth side of the multi-well plate. At least one leg (504, 506) comprises a ramp (507, 508) to apply both sideways force towards the second stop and downward force on the skirt of the multi-well plate (as shown in FIGS. 5(e)-(i)).

Figure 5C:
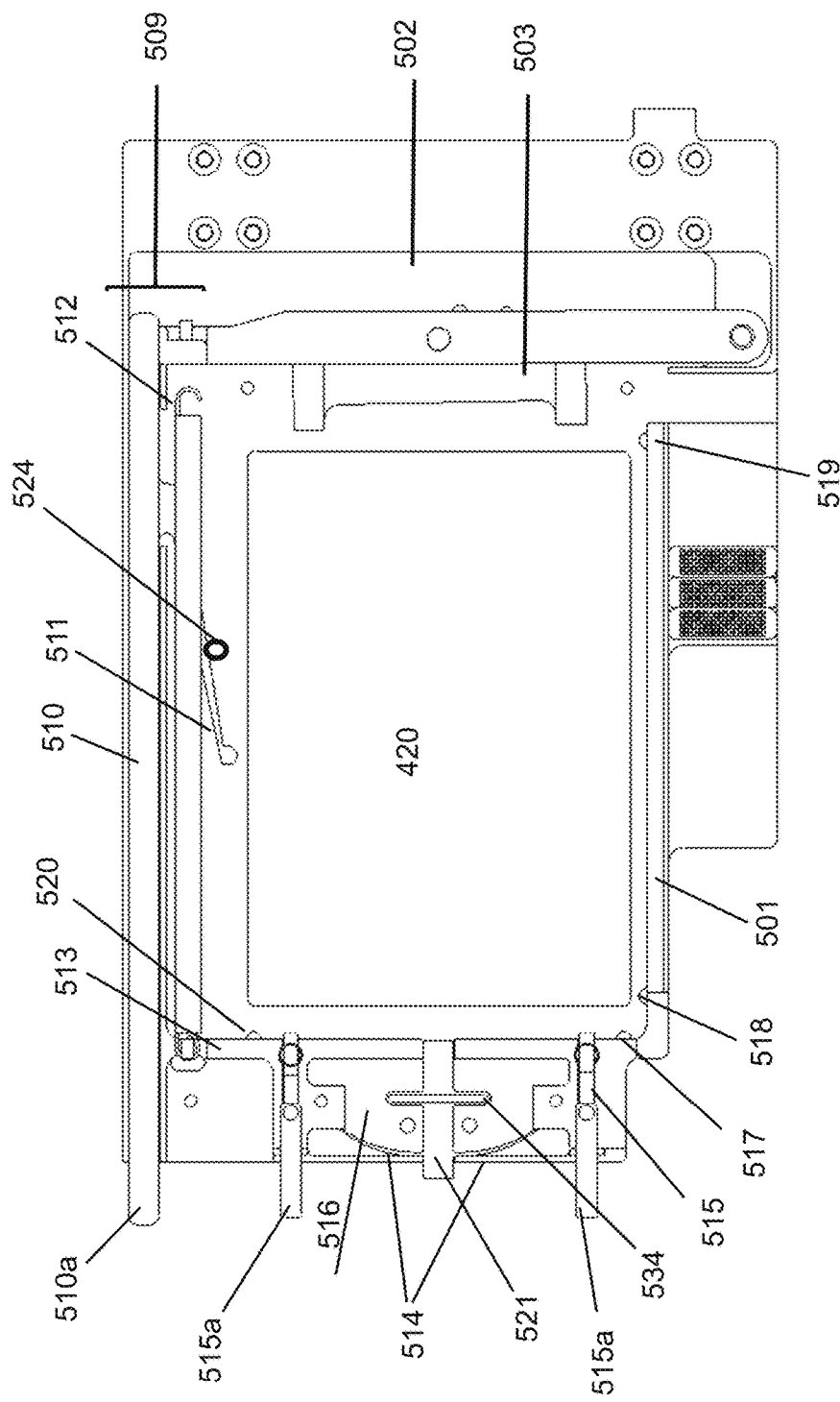
Figure 5D:
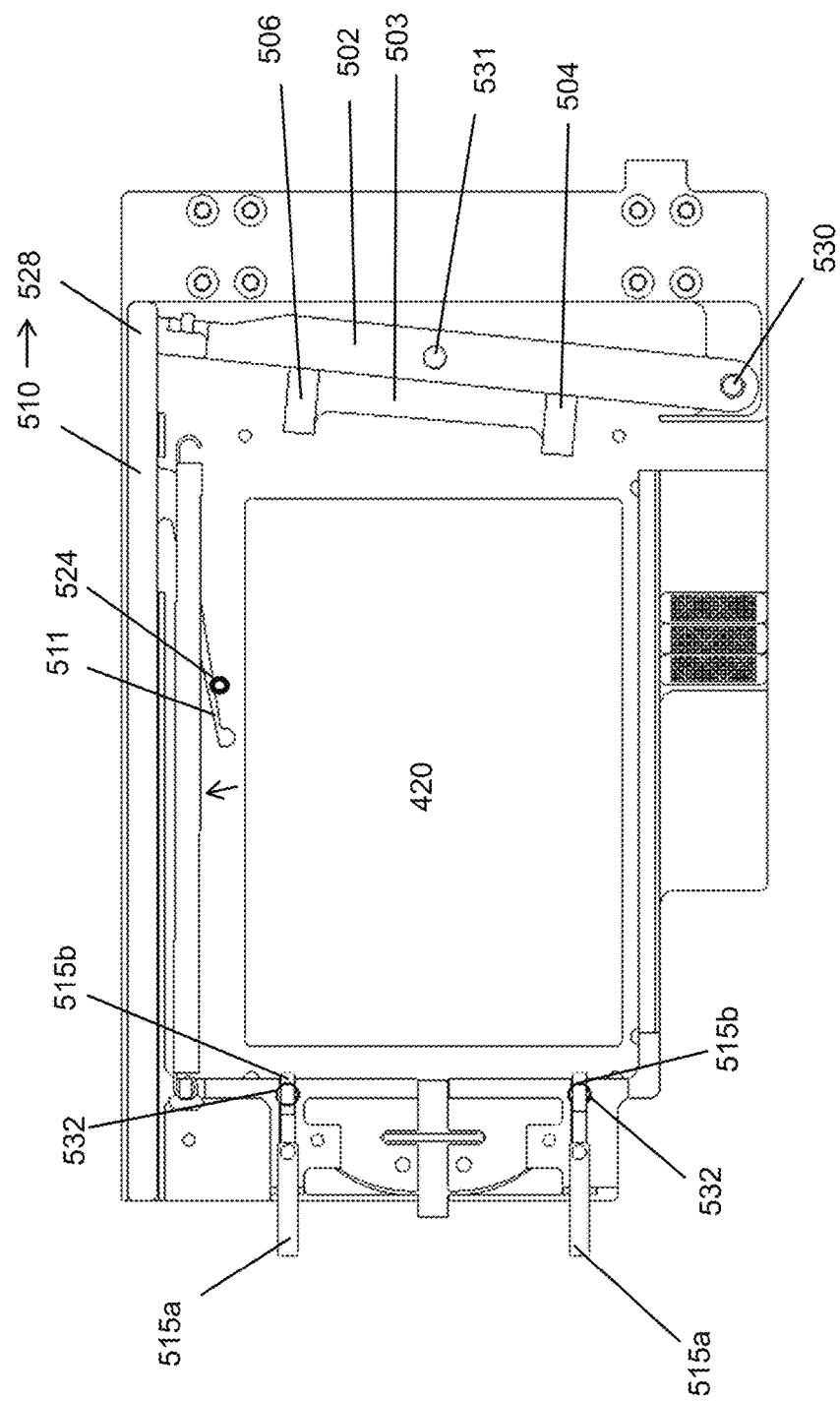
Figure 5I:
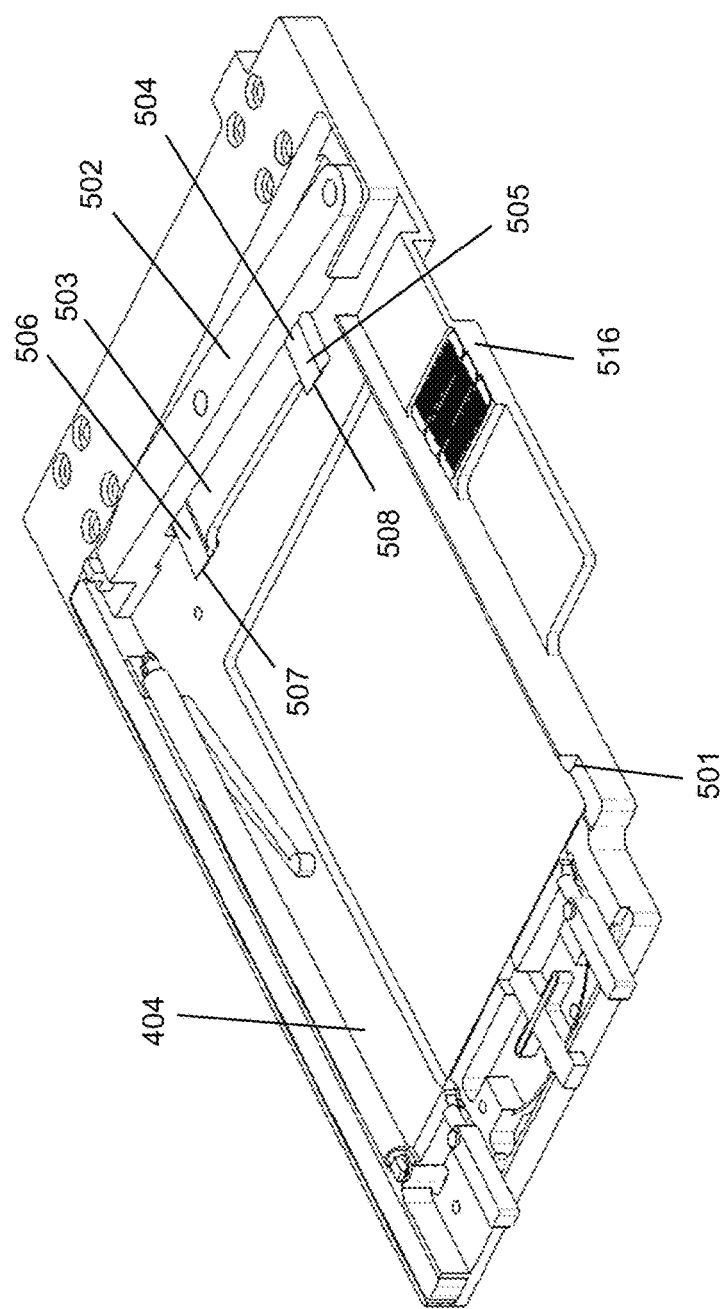
Figure 5J:
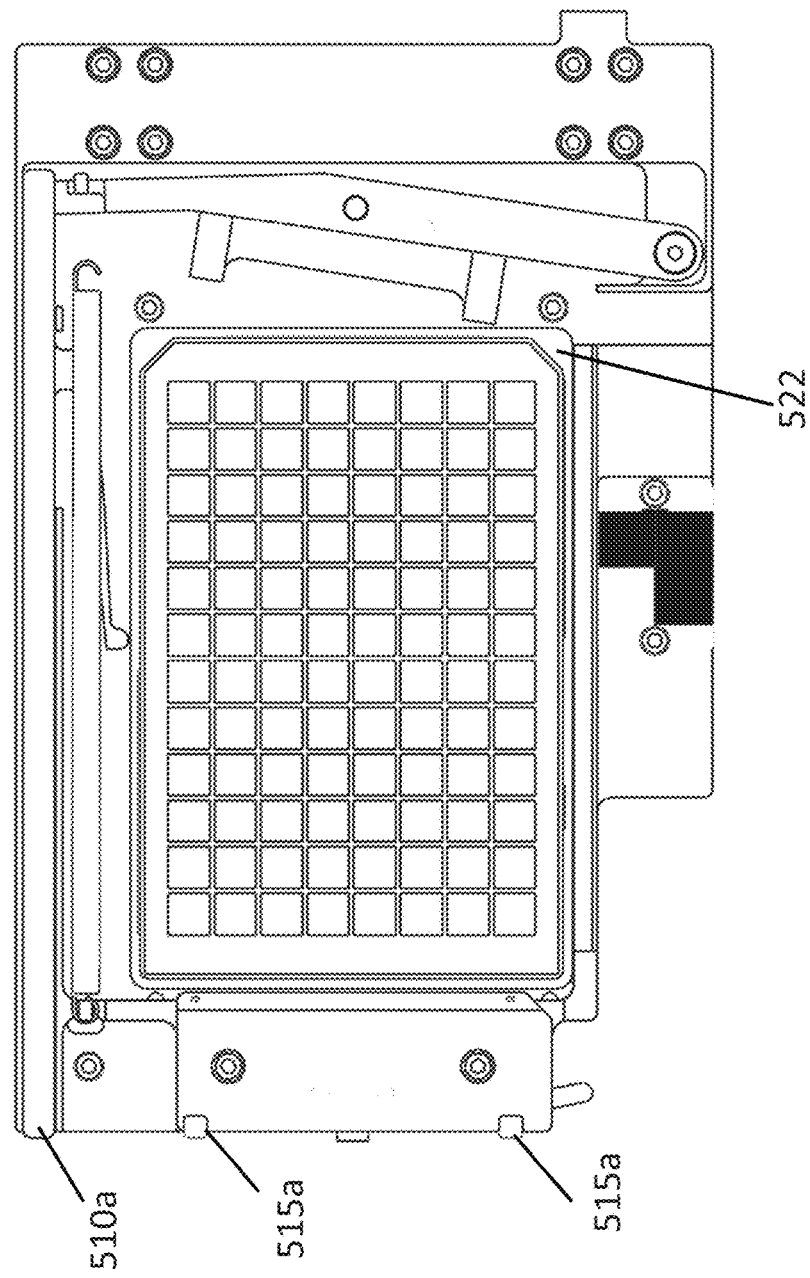

The first latching member 509 comprises an actuating rod (510), which is biased to the clamping position by a spring (512) and in the clamping position extends past one edge of the plate carriage (as shown in FIG. 5(c). During loading and unloading of plates, as the plate carriage 404 is moved into alignment with a plate elevator, the extended portion 510a of actuating rod (510) is pushed against a physical stop in the housing, e.g., the rear wall of drawer 240 or housing rear 235, which pushes extended portion 510a of rod (510) into the carriage, as best shown in FIG. 5(d) where rod 510 is not yet engaged and FIG. 5(e) where rod 510 is pushed. It is noted that when plate carriage 404 is moved against the physical stop, rod 510 and both biased clamps 515 are pushed, FIGS. 5(d) and 5(i) only show the retraction of rod 510 for clarity. The movement of rod (510) forces the pedal 511 to retract toward rod 510 to make room for plate 426. As shown in FIG. 5(c), pedal 511 is a cantilever type arm that is attached to rod 510 and has the ability to flex like a spring. A fulcrum 524 fixedly attached to plate carriage 404 forces pedal 511 to retract or move in the direction of the arrow shown in FIG. 5(d) as rod 510 is pushed inward. Fulcrum 526 can also be located on the sheath 526 that covers first latch member 509, as best shown in FIG. 5(a). Plate clamp arm 502 is connected preferably pivotally at one end 528 to rod 510, and connected preferably pivotally at the opposite end 530 to plate carriage 404. Bracket 503 is pivotally connected to plate clamp arm 502 at pivot point 531. As best shown in FIG. 5(d), as rod 510 is pushed inward pedal 511 and plate clamp arm 502 with bracket 503 are retracted or moved away from opening 420.

An advantage of connecting bracket 503 pivotally to plate clamp arm 502 is that bracket 503 can rotate, preferably slightly relative to plate clamp arm 502, so that both legs 504 and 506 of bracket 503 can make contact with plate 426 during the latching process.

As discussed above, when plate carriage 404 is moved against the physical stop, rod 510 and both biased clamps 515 are pushed. As extended portions 515a of biased clamp 515 are pushed inward, this action lifts the biased end 515b upward against the force of spring 532. As biased end 515b is lifted into an open position, it is sized and dimensioned to accept skirt 522 of plate 426, and as biased clamp 515 is released spring 532 forces biased end 515b downward and clamp onto skirt 522 to hold tray 426 against upward motions.

The apparatus further comprises an ejector (516) to release plate 426 from the latching mechanism. Ejector 516 has an extended actuating element (521) and like actuating rod (510) also is pushed against a stop in the instrument as the plate carriage is placed in alignment with the plate elevators, such that the ejector moves the multi-well plate 426 away from the second stop 513. The ejector 516 is preferably spring-loaded by springs 514 and it optionally includes an over-travel preventer 534. Ejector 516 when activated pushes tray 426 away from stop 513, and when ejector 516 is activated rod 510 and biased clamps 515 are also moved to the open position, so that tray 426 can be pushed away from stop 513 and biased claim ends 515b. Over-travel preventer 534 can elastically deform to absorb some of the motion of ejector Movement of the carriage plate 404 away from the plate loading/unloading position (i.e., in alignment with the plate elevators), reverses them movement of rod (510) and ejector (516) and resets the latching mechanism into the latched configuration.

Engagement of a multi-well plate 426 with the plate latching mechanism to lock the plate 426 in the plate carriage 404 is illustrated in FIGS. 5(i)-(m). FIG. 5(i) is similar to FIG. 5(d) showing the first latch member 509 with pedal 511 retracted and arm 502/bracket 503 in the open position. The latching mechanism remains unengaged and in the open position in FIG. 5(j), allowing a multi-well plate 426 to be placed over opening 420 within the plate carriage 404. In the open configuration depicted in FIG. 5(j), pedal 511, clamp arm 502, bracket 503 and biased clamp 515 are biased away from opening 420 to allow a plate 426 to be loaded into the plate carriage 404. As shown in FIG. 5(j), extended portions 510a and 515a are all pushed inward by motion of plate carriage 404 against a back stop such as the back side of drawer 240 or housing rear 235.

Figure 5K:
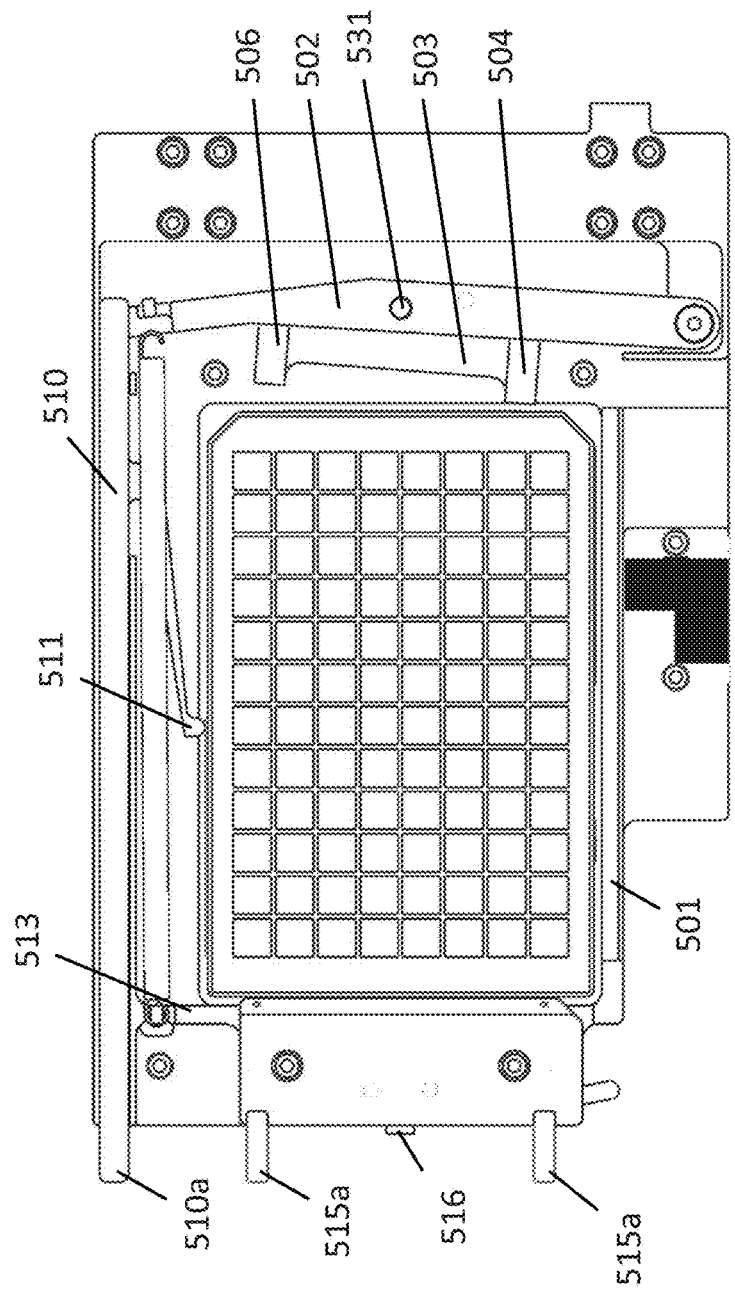

When a plate 426 is placed into the plate carriage 404 as shown in FIG. 5(k) and plate carriage 404 moves away from the back stop, pedal 511 moving away from fulcrum 524 and outward to push and bias tray 426 against first stop 501. Plate clamp arm 502 also moves with rod 510, allowing bracket 503 to push tray 426 against second stop 513. As shown in FIG. 5(k), only leg 504 is contacting tray 426; however, due to the pivoting connection at pivot point 531, second leg 506 would automatically and quickly contact tray 426 as bracket 503 rotates about pivot 531. Biased clamp 515, which is preferably spring loaded by springs 532, engages the plate skirt 522 of the multi-well plate 426 on the second side of the plate as shown in FIG. 5(l), bracket 503 also engages with and pushes down on the plate skirt 522. As discussed above, legs 504 and 506 of bracket 503 has ramp 507, 508 and angled as shown. As legs 504 and 506 pushes tray 426, ramp 507, 508 contact skirt 522 and pushes tray 426 in two directions: toward second stop 513 and downward. As shown in FIG. 5(*m*), biased clamp 515, engages with plate skirt 522.

In a preferred embodiment the plate carriage 404 also includes an optical focusing mechanism used by an optical sensor in the apparatus, such as the light detectors within light detection system 110 described above to measure contrast and focus. The optical focusing mechanism includes at least two, or preferably at least three, patterned surfaces at different heights relative to the plate carriage and, consequently, to a target surface for focusing (i.e., the bottom of the wells of a 96-well plate 426 held in the plate carriage 404). The invention includes a method for imaging the plurality of surfaces and, based on the image, calculating the magnitude and direction of the image adjustment needed to bring the target surface into focus. In one embodiment, contrast values are calculated for the image of each surface and the focus height is determined as the height at which the change in contrast with change in height is minimized or, alternatively, falls below a predetermined threshold value.

In one embodiment, the plate carriage includes at least three patterned surfaces each at differing heights relative to the plate carriage. Two alternative embodiments of an optical focusing mechanism are shown in FIG. 6(*a*)-(*b*). In certain preferred embodiments the surfaces have patterns of differential transparency (e.g., patterns etched or cut into a non-transparent substrate or a patterned non-transparent ink or film printed on a transparent surface) so that the pattern can be imaged using light transmitted through the substrate. In alternative embodiments, the surfaces/patterns are not transparent and the patterns are imaged using a light source that reflects light off the surface.

The focusing mechanism includes at least a higher, middle and lower patterned surface spaced apart from the optical sensor, wherein the middle patterned surface and the target surface are aligned to substantially the same planar level, wherein a first distance between the higher and middle patterned surfaces and a second distance between the middle surface and lower patterned surface are substantially equal, and wherein the optical sensor and the patterned surfaces are moved relative to each other until a difference between a first pair of contrast values between the higher and middle pattern and a second pair of contrast values between the middle pattern and the lower pattern is less than a predetermined value of about ±2.0 dimensionless units, as explained below. This difference may be ±3.0 or ±4.0, or as low as ±1.0. Higher value of contrast differences allow easier but less accurate focusing, and lower value of contrast differences yields more difficult but more accurate focusing.

As shown in FIGS. 6(*a*)-(*b*), the mechanism preferably includes a plurality of patterned surfaces, e.g., at least two and optionally three patterned surfaces (601-603), and the patterned surfaces comprise substantially the same pattern, e.g., a grid pattern. The patterned surfaces are preferably adjacent to one another in a grouping. In the embodiment shown in FIG. 6(*a*), the mechanism also includes an unpatterned surface 604. Preferably, each of the patterned surfaces are located on parallel planar planes. In a preferred embodiment, the middle patterned surface is at a height effectively equivalent to a focus position of a well in multi-well tray 426 filled with a predetermined amount of fluid. The lower patterned surface is at a height that is about 0.25 mm below the middle patterned surface and the upper patterned surface is at a height that is about 0.25 mm above the middle patterned surface. In one embodiment, the lower patterned surface is at a height of about 4-4.75 mm above the plate carriage (i.e., above the carriage platform that the plate rests on). Preferably, the lower patterned surface is at a height of about 4.5-4.7 mm above the plate carriage, and most preferably, the lower patterned surface is at a height of about 4.6-4.7 mm above the plate carriage. The middle patterned surface is at a height of about 4.5-5.0 mm above the plate carriage, preferably, about 4.7-4.9 mm above the plate carriage, and most preferably, about 4.7-4.8 mm above the plate carriage. And the higher patterned surface is at a height of about 4.75-5.10 mm above the plate carriage, preferably about 4.8-5.0 mm above the carriage platform, and most preferably about 4.85-4.95 mm above the plate carriage. It is noted that any one of the surfaces 601, 602 and 603 can be the middle patterned surface, the higher pattern surface, or the lower pattern surface. In a preferred embodiment, the optical focusing mechanism is adjacent to the plate carriage.

Therefore, the invention provides a method for focusing an optical sensor to a target surface comprising the steps of (a) providing at least a higher, middle and lower patterned surface 601-603, wherein the middle patterned surface and the target surface are at the same focal height and wherein a first distance between the higher and middle patterned surfaces and a second distance between the middle surface and lower patterned surface are substantially equal; (b) obtaining a first contrast value difference between the higher and middle patterned surfaces with the optical sensor; (c) obtaining a second contrast value difference between the middle and lower patterned surfaces with the optical sensor; and (d) comparing the first and second contrast value differences and determining if the target surface is in focus and/or determining the magnitude and direction of focus adjustment needed to place the target surface in focus.

During operation, the plate translation stage 403 translates the plate carriage 404 to position the optical focusing mechanism over the contact mechanism shown in FIGS. 7(*a*)-7(*c*)(1), which includes a light source, such as light outlets 725-728 shown in FIG. 7(*c*)(1). Light outlets 725-728 can be connected to a single light emitting diode (LED) or each light outlet may have its own LED or other light sources. The light source is illuminated and a beam of light is shown on the underside of the optical focusing mechanism, more specifically under surfaces 601-603. Preferably, light outlets 725-728 provides even lighting for surfaces 601-603. An optical sensor or camera in the light detection subsystem 110 therefore, images the optical focusing mechanism, calculates the differences in contrast values described above, and determines if the target is in focus and/or determines the magnitude and direction of the focus adjustment needed to place the target surface in focus. Based on the calculation, the focus of the optical sensor is adjusted accordingly, either manually or automatically, e.g., through the use of a motorized focus adjustment. Preferably, the method also includes the steps of adjusting the distance between the optical sensor and the target surface and repeating the steps of obtaining the first and second contrast values and comparing those contrast values until a difference between the first and second contrast values are less than a predetermined value. A suitable calculation to determine the contrast value is to take a region or interest (ROI) of an image that is covered by the dot pattern of the focus target, e.g., surface 601, 602 or 603 or a portion thereof. The average and the standard deviation of all of the pixels within that ROI are measured. The average (AVG) and standard deviation (StDEV) to calculate the contrast value (% CV) of that ROI are measured or ascertained.

$$\% \, CV = (StDEV/AVG) \times 100$$

Then the % CV for each ROI (high and low) are then subtracted to create the difference value that is reported to the operator. % CV as shown above is a unit-less or dimensionless value.

A preferred predetermined value of the difference in % CV contrast values is determined as ±2.0 experimentally by comparing ECL value as a function of defocus from nominal. The magnitude of this difference may change depending on the contrast function. A certain amount of defocus was acceptable without affecting ECL. The preferred value of ±2 is within this range. A smaller value, e.g., ±1.5 or ±1.0 would be more accurate but also more difficult to achieve during the focus operation. A larger value, e.g., ±3.0 or ±4.0 would be less accurate but easier to achieve. One of ordinary skilled in the art may balance accuracy and operational difficulty according to the teachings of the present invention. Differences in contrast values between ±1.0 and ±4.0 are within the scope of the present invention.

Other methodology of calculating or ascertaining contrast values, such as those discussed in "Contrast in Complex Images" by Eli Peli, published in the Journal of the Optical Society of America, No. 10, October 1990, at pages 2032-2040, can be used. This reference is incorporated by reference herein in its entirety.

Additionally, plate carriage 404 contains a plurality of reference elements. One reference element comprises an electrically conductive bottom surface 536 disposed on a bottom surface of plate carriage 404, as shown in FIG. 5(n), which is used, during setup of the apparatus, to train the positioning of the contact mechanism used to contact the bottom of plates 426 held in the plate carriage 404. The contact mechanism, described in more detail hereinbelow, includes a series of spring loaded contact members and can be raised to contact a plate 426's bottom surface, e.g., to initiate an ECL measurement. As shown in FIG. 5(n), the conductive bottom surface 536 is on the underside of the plate carriage 404 and it is configured to be at the same height as a plate bottom when a plate 426 is latched in the plate carriage 404. During apparatus setup or adjustment, the contact mechanism is raised until it reaches a height where the contact members touch surface 536, as detected by electrically measuring the drop in resistance between contact members, signaling that the contact members have properly touched conductive surface 536 and would properly contact the plate bottoms during ECL measurements. This measured height is used to set the contact mechanism height for contacting plates 426 held in the plate carriage 404.

Still further, the plate carriage 404 comprises another reference element (depicted in FIG. 5(c) as semicircular apertures cut into plate carriage 404, i.e., elements 517-520). A light source, such as light outlet or LED 722 in the contact mechanism is projected through each aperture 517-522. Plate translation stage 403 moving in the horizontal plane discussed above position each aperture 517-522 above light outlet 722 shown in FIG. 7(c)(1). The light projected through each aperture is imaged by the light detector in light detection system 110 to reference the location of the plate carriage 404 in the x-y space of the horizontal plane relative to other components of the apparatus. In a preferred embodiment, the reference elements comprise one or more indentations or cut-outs, e.g., on the edge of the plate platform, e.g., as shown in FIG. 5(c), at the two ends of reference surfaces/stops (501) and (503). Advantageously, the elements may also be imaged to confirm if the plate is in the correct orientation.

Figure 7A:
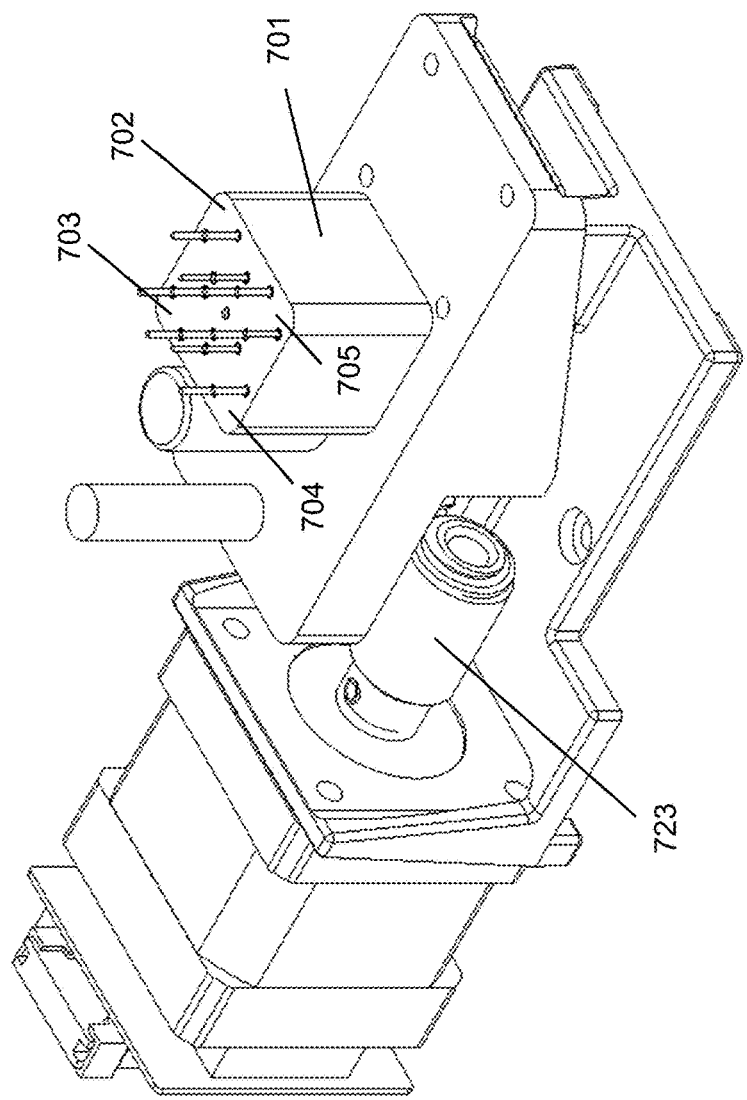
FIGS. 7(*a*)-(*l*) show detailed views of the plate contact mechanism.
Figure 7B:
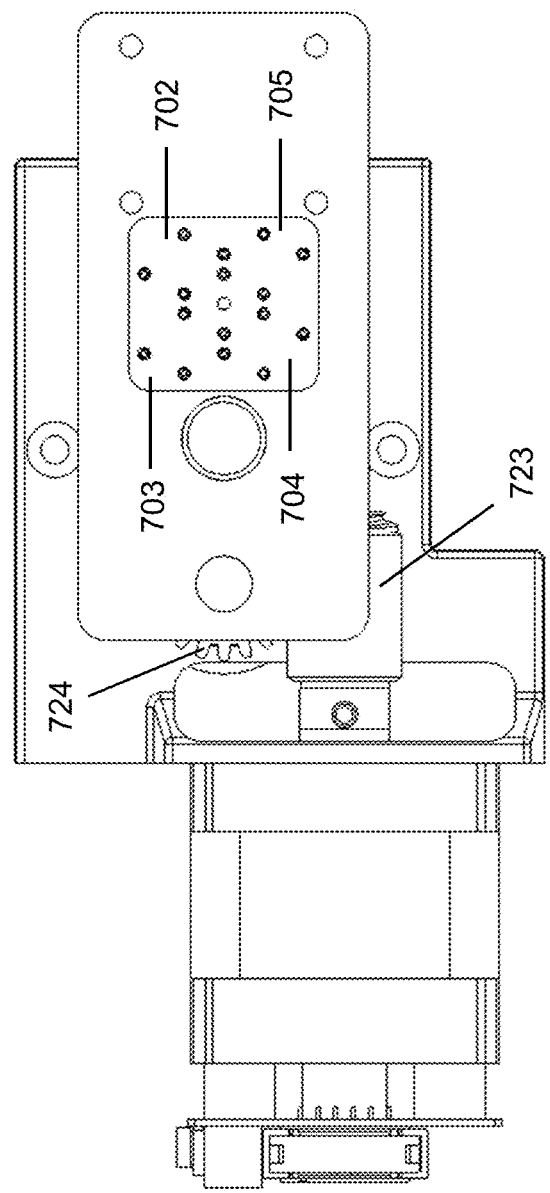
Figure 7H:
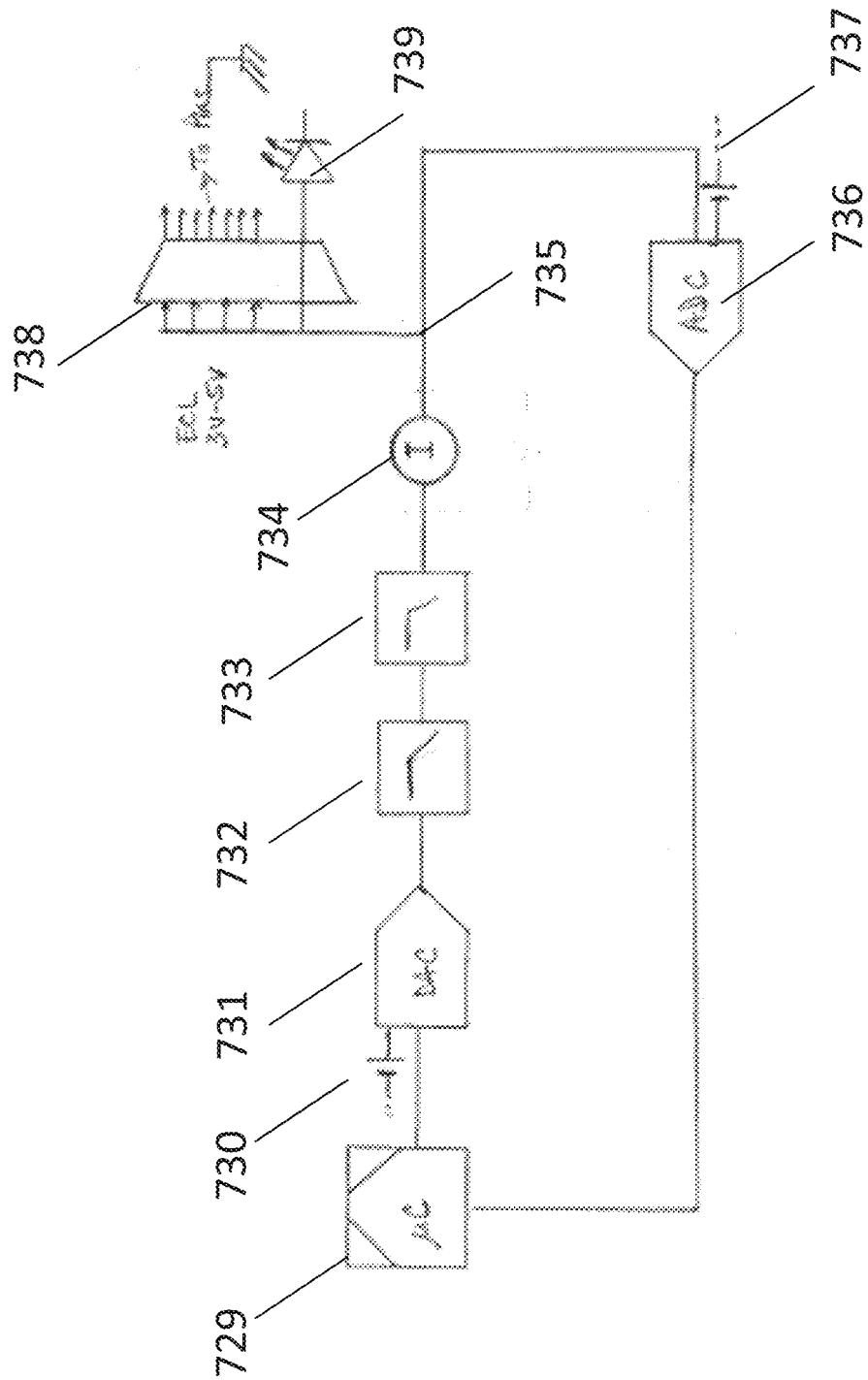

Light outlet 722 and light outlets 725-728 are preferably illuminated by a single LED. A suitable LED can be connected to light pipes or waveguides to the light outlets. A suitable LED can have different intensity outputs depending on the voltage applied. In one example, as illustrated in FIG. 7(h), LED 739 is connected to multiplexer 738. Microprocessor 729 can instruct multiplexer 738 to apply a first voltage to LED 739 to activate light outlet 722 and to apply a second voltage to LED 739 to activate light outlets 725-728. Alternatively, multiple LEDs can be used for the light outlets.

The plate handling subassembly also includes one or more shipping locks to lock the plate carriage in place during shipping, discussed above and best illustrated in FIG. 4(e). In a preferred embodiment, the shipping locks include solenoid driven pin 411 on removable drawer 240 being received in hole 412 on plate translation stage 403. The plate carriage 404 rides on rails 422, 424, and preferably comprises a clamp to lock the carriage in place. Still further, the plate carriage 404 includes a plate orientation sensor, such as an accelerometer or electronic leveler, to ensure that a multi-well plate 426 placed on the plate carriage 404 is in the correct orientation.

The plate handling subassembly 120 also includes a plate contact mechanism that includes electrical contact probes mounted onto a plate contact elevator for raising the probes to contact electrical contacts on the bottom of a multi-well plate 426 discussed above, that are in turn connected to electrodes in the wells of the plate. The contact probes are used to apply the electrical potentials to electrodes in one or more wells of a multi-well plate 426. The plate contact mechanism and the imaging apparatus are in alignment, such that the electrical contact is made with the well or set of wells that is/are directly under, and in the imaging field of, the imaging apparatus. The contact mechanism is shown in FIG. 7(a)-(b) and includes a contact mechanism platform 701 comprising four interrogation zones 702-705, wherein each zone includes a pair of electrical contact probes to conduct a voltage potential to the interrogation zone. Preferably, interrogation zones 702-705 are arranged in quadrants or 2×2 matrix. However, interrogation zones can be arranged in a linear manner or in any P×Q matrix, wherein P and Q are integers and can be different from each other. As discussed in more detail below, multi-well plate 426 usable in inventive instrument 100 can be arranged in a M×N matrix, where the M×N matrix is larger than the P×Q matrix. As discussed above, P×Q matrix can be 12×8, 24×16, 48×32 wells or any number of wells.

The apparatus also includes a controller operatively connected to a voltage source, wherein the voltage source is connectable to one or more pairs of electrical contact probes, and a multiplexer connected to the controller and to the voltage source for selectively connecting the voltage source to the pair of electrical contact probes of a single interrogation zone or connecting the voltage source to the pairs of electrical contact probes of more than one interrogation zone. A block diagram showing the components of the controller is shown in FIG. 7(h), including microprocessor 729, connected to power source 730 and digital analog converter 731, which is connected to low pass filters 732 and 733, current monitor 734, another optional power source 737, and analog digital converter 736, and a multiplexer 738. The controller is also operatively connected to an LED 739, which is a component of the contact mechanism, discussed above.

The multiplexer 738 controlled by processor 729 directs the application of potential as identified above based on the type of plate used in the instrument. If the multi-well plate 426 is configured to be analyzed one well at a time, referred to herein as a single-well addressable plate, wherein a well of a plate corresponds to a zone of the contact mechanism platform, the multiplexer 738 will direct the selective application of potential by electrically isolating each zone and selectively applying a potential only within a first zone. If, on the other hand, the multi-well plate is configured to be analyzed two or more wells at a time, referred to herein as a multi-well addressable plate, the multiplexer 738 will direct the selective application of potential by electrically connecting two or more zones and selectively applying a potential within those two or more zones. In one embodiment, the plates comprise a bar code that includes plate configuration information and the apparatus 100 comprises a bar code reader 238 that reads the plate configuration information and identifies the type of plates positioned in the stacker.

In a preferred embodiment, the apparatus includes a plurality of interrogation zones 702-705 that are arranged in a P×Q matrix. Preferably, the P×Q matrix is a 2×2 matrix. The pairs of electrical contact probes on the plate contact mechanism platform 701 preferably comprise upstanding pins, e.g., spring-loaded pin. Still further, the apparatus preferably further includes an optical sensor, such as the light detectors in the light detection system 110, positioned above the platform 701 and the platform 701 includes a first alignment mechanism comprising a light source, such as light outlet 722 projecting from the platform toward the optical sensor to align the platform 701 relative to the optical sensor. In one embodiment, the light source (e.g., an LED or other type of light bulb) is positioned under and shines light through an aperture in the contact mechanism, e.g., through aperture (722) which is centered in platform (701) as shown in FIG. 7(c)(1). The apparatus also preferably includes a second alignment mechanism comprising a plurality of apertures located on the plate carriage frame (e.g., elements 517-520 shown in FIG. 5(c)) and the light source 722 from the platform 701 can be illuminated through these apertures and detected by the optical sensor to further align the plate carriage frame with the platform 701. The plurality of apertures can be positioned on at least two sides of the plate carriage frame (see description above). Moreover, the apparatus further preferably includes a third alignment mechanism comprising an electrical conductive surface located on the plate carriage frame (e.g., surface 536 in FIG. 5(n)) such that when the electrical contacts on the platform are brought in contact with the electrical conductive surface electrical current flows among the electrical contacts on the platform to indicate a predetermined distance between the electrical contacts and the plate carriage frame. The apparatus preferably includes a fourth alignment/focusing mechanism comprising patterned focusing targets (e.g., surfaces 601-603 in FIGS. 6(a) and 6(b)) and the contact mechanism platform includes one or more light sources for passing light through the patterns to enable imaging of the patterns, discussed above. The light source(s) may be a light source under aperture (722) as described above. Optionally, a plurality of light sources (e.g., LEDs or other types of light bulbs) may be used to generate a wider and more even light field, e.g., the four LEDs (725-728) embedded in the plate contact mechanism platform as shown in FIG. 7(c)(1).

In a preferred embodiment, the apparatus is adapted to interrogate samples contained in a multi-well plate, wherein the multi-well plate comprises a plurality of wells arranged in an M×N matrix, and the apparatus includes a carriage frame configured to support the multi-well plate, wherein the carriage frame is movable relative to a contact mechanism platform comprising a plurality of interrogation zones, wherein each interrogation zone comprises at least a pair of electrical contact probes to apply a voltage potential to at least one well. The apparatus also includes a controller operatively connected to a motor to move the carriage frame relative to the platform and operatively connected to a voltage source, wherein the voltage source is connectable to one or more pairs of electrical contacts, and a multiplexer connected to the controller and to the voltage source for selectively connecting the voltage source to the pair of electrical contact probes of a single interrogation zone or connecting the voltage source to at least one pair of electrical contact probes of more than one interrogation zones. Preferably, the interrogation zones are arranged in a P×Q matrix and the M×N matrix is larger than the P×Q matrix, which can be a 2×2 matrix. Preferably, each interrogation zone is sized and dimensioned to interrogate one well on multi-well plate 426.

Preferably, the electrical contact probes on the contact mechanism platform include a plurality of working electrode contact probes that are selectively connected by the controller to the voltage source to determine the number of wells to interrogate. In one embodiment, a working electrode probe is connected to the working electrode in one well, or alternatively, one working electrode probe is connected to the working electrode in a plurality of wells. The working terminals electrode probes that are not connected can be electrically isolated in the multiplexer when not in use, thereby allowing a plurality of working electrode probes (e.g., 4 probes) to be used to apply potential to a plurality or working electrodes in a plurality of wells, one well at a time (e.g., applying potential to a group of 4 wells, one well at a time). The electrical contacts on the platform can further comprise a plurality of counter electrode probes that are electrically connected to at least one electrical ground. In one embodiment, the bottom electrical contacts of the multi-well plate that are connected to the counter electrode probes on the platform for a plurality of wells are electrically connected. Alternatively, the bottom electrical contacts of the multi-well plate that are connected to the counter electrode probes on the platform for all the wells are electrically connected. Still further, the bottom electrical contacts of the multi-well plate that are connected to the counter electrode probes on the platform for at least one well can be electrically isolated. The controller can interrogate P×Q or fewer number of wells simultaneously.

Referring to FIGS. 7(c)(2)-(g), the contact mechanism platform 701 includes a plurality of working contact probes 706-713 and counter contact probes, 714-721. As shown in FIG. 7(c)(2), if the controller 729 is configured to electrically connect two or more interrogation zones, then the instrument 100 selectively applies a potential within two or more zones, e.g., zones 703 and 704, thereby applying a potential across working electrode contact probes 706 and 710 and 709 and 713, respectively and connecting counter electrode contact probes 714-717 and 718-721. The connections of the counter electrodes at platform 701 and plate 426 are discussed below. Also as discussed below, only one working contact electrode and one counter contact electrode are necessary. Two of each are connected to provide a redundancy for the system, so that an ECL signal is generated even when one electrode fails.

Alternatively, if the switching mechanism is configured to electrically isolate each zone then the instrument selectively applies a potential within a first zone, e.g., as in FIG. 7(d), wherein zone 703 is isolated and an electrical potential is applied across working electrode contact probes 706 and 710. In one embodiment, all counter electrode contact probes 714-717 and 718-721, which are connected to ground, are electrically connected at platform 701. As discussed below in connection with FIG. 7(k), the counter electrode contact probes for each well are isolated by the counter electrodes on the bottom of plate 426. In the example shown in FIG. 7(d), the well directly above zone 703 has a counter electrode that connects to counter electrode contact probes 718 and 719, but isolates from the other counter electrode contact probes on platform 701. Alternatively, the counter electrodes for each interrogation zone can be isolated at platform 701.

Similarly, FIGS. 7(e)-(g) illustrate how the contact mechanism is configured to apply a potential within a first zone, 702 (FIG. 7(e)), 705 (FIG. 7(f)), and 704 (FIG. 7g), and a potential is applied across working contact probes 707 and 712 (in FIG. 7(e)), 708 and 711 (in FIG. 7(f)), or 709 and 713 (in FIG. 7(g)), respectively, while counter contact probes 714-717 and 718-721 are electrically connected at platform 701, but the counter contact probes for each interrogation zone are isolated by the counter electrode on the well on plate 426 directly above each interrogation zone. Preferably, the contact probes are each independently spring-loaded contacts members, e.g., contact pins.

In a preferred embodiment, the multi-well plate 426 comprises bottom electrical contacts on a bottom surface of the plate for each well, wherein the bottom electrical contacts are configured to contact the pair(s) of electrical contact probes on the platform 701. The bottom electrical contacts include counter electrode contacts that are connected to counter electrodes in the wells of the plate and working electrode contacts that are connected to working electrodes in the wells of the plate. Each well includes at least one working and one counter electrode, which depending on the plate format, may be electrically connected (bussed) or electrically independent of the working and counter electrodes in other wells of the plate.

A non-limiting set of exemplary bottom electrical contact patterns are shown in FIGS. 7(i)-(l), wherein FIG. 7(i) shows the pin contact configuration of platform 701 substantially similar to FIG. 7(c)(2). FIG. 7(k) shows an overlap of the bottom electrical contacts under exemplary four wells that overlay interrogation zones 702-705. Each well has bottom counter electrode 740 having an exemplary "Z-shape" and two working electrodes 742 and 744. Bottom counter electrodes 740 are not electrically connected to each other, and hence the counter electrodes for each well or each interrogation zone are separated or isolated at plate 426.

For zone 703, Z-shape bottom counter electrode 740 connects to counter electrodes 718 and 719. Bottom working electrodes 742 and 744 are connected to working electrodes 710 and 706, respectively.

For zone 705, Z-shape bottom counter electrode 740 connects to counter electrodes 720 and 721. Bottom working electrodes 742 and 744 are connected to working electrodes 711 and 708, respectively. Zones 702 and 704 are similarly connected.

The next electrical connection is to the inside of the well itself. As illustrated in FIG. 7(l), each well in this example has well working electrode 750 and well counter electrodes 752 and 754. Here, well working electrode 750 has a Z-shape and connects to both bottom working electrode 742 and 744, and well counter electrodes 752 and 754 are connected to bottom counter electrode 740.

For zone 705, working electrodes 711 and 708 on platform 701 are connected to bottom electrodes 742 and 744 and well working electrode 750 for each well. Counter electrodes 720 and 721 on platform 701 are connected to bottom counter electrode 740 and well counter electrodes 752 and 754 for each well. The Z-shapes for bottom electrode 740 and well electrode 750 are designed to ensure sufficient electrical contact. Any shape can be used and the present invention is not limited to any particular shape.

As shown in the above discussion, each well and each interrogation zone has two working electrodes, e.g., 708 and 711 for zone 705, and two counter electrodes, e.g., 720 and 721 for zone 705. Both working electrodes and both counter electrodes are electrically connected to a well as shown above. Only one pair of working and counter electrodes is necessary to conduct ECL potential to a well. The other pair is for redundancy, in case one or more electrode malfunctions.

It is further noted that in the example discussed above in connection with FIGS. 7(i), 7(k) and 7(l) where each well can be interrogated individually, the working electrodes for each interrogation zone and well are isolated at platform 701 and multiplexer 738, and the counter electrodes for each interrogation zone and well are isolated at plate 426 and its bottom electrodes and well electrodes.

FIG. 7(j) illustrates an example where four wells overlaying interrogation zones 702-705 can be interrogated at the same time using the contact pins or electrodes from the same platform 701. As shown, this multi-well plate 426 has bottom working electrode 760 overlaying working electrodes 707, 708 and 709. Tray 426 also has bottom counter electrode 762 overlaying at least counter electrode 719, 720, 715 and 716. Bottom working electrode 760 and bottom counter electrode 762 are electrically connected upward to all four wells. Activating one or more working electrodes 707, 708 and 709 and one or more counter electrodes 719, 720, 715 and 716 would provide an ECL potential to all four wells. Redundancy is also provides by the plurality of available working and counter electrodes.

According to an embodiment of the present invention, the plate bottom comprises internal electrical contacts conduits connected to the bottom electrical contacts to conduct the voltage potential to within the wells. In one embodiment, the bottom electrical contacts for at least one well are electrically isolated from the bottom electrical contacts for adjacent wells and optionally, the internal electrical contacts conduits for at least one well can be electrically isolated from the bottom electrical contacts for adjacent wells. Reference is made to U.S. Pat. No. 7,842,246 and U.S. Application No. 20040022677 (both entitled "Assay Plates, Reader Systems and Methods for Luminescence Test Measurements", filed on Jun. 28, 2002, hereby incorporated by reference), which discloses additional embodiments of plate bottoms that can be interrogated by the contact mechanism disclosed herein.

Therefore, the invention provides a method for interrogating samples contained in a multi-well plate having a M×N matrix of wells comprising the steps of (a) providing a plate contact mechanism platform having a plurality of interrogation zones, (b) providing at least a pair of electrical contact probes (e.g., a working electrode contact probe and a counter electrode contact probe) for each interrogation zone, wherein each interrogation zone is adapted to interrogate a single well, (c) selectively applying a voltage potential to: (i) one interrogation zone to interrogate one or more wells simultaneously or (ii) a plurality of interrogation zones to interrogate a plurality of wells, and (d) moving the multi-well plate relative to the platform to interrogate additional wells. A single well can be interrogated or a M×N number of wells can be interrogated (wherein M×N is larger than the P×Q matrix). The method can also include the step of (e) controlling the application of voltage potential in step (c) by selecting at least one positive active contact probe (e.g., the working electrode probe) of the pairs of the electrical contact probes on the platform to connect to the voltage potential. Step (e) can also include the step of electrically isolating at least one positive active contact probe not connected to the voltage potential. The method can also include step (f), providing bottom electrical contacts on a bottom surface of the multi-well plate and optionally, (g) electrically isolating at least one ground contact probe (e.g., the counter electrode probe) from the bottom electrical contacts. Optionally, all ground contact probes from the bottom electrical contacts are isolated from each other.

As described above, the apparatus can be used to measure luminescence from two alternative types of multi-well plates, a single-well addressable plate (i.e., a plate that is interrogated by the apparatus one well at a time), and/or a multi-well addressable plate (i.e., a plate that is interrogated by the apparatus one sector at a time, wherein a sector is a grouping of adjacent wells). Various types of multi-well plates including single-well and multi-well addressable plates are described in U.S. Pat. No. 7,842,246 and U.S. Application No. 20040022677 (both entitled "Assay Plates, Reader Systems and Methods for Luminescence Test Measurements", filed on Jun. 28, 2002, hereby incorporated by reference). The plates of the invention include several elements, including but not limited to, a plate top, a plate bottom, a plurality of wells, working electrodes, counter electrodes, reference electrodes, dielectric materials, electrical connections, conductive through holes, and assay reagents. The wells of the plate are defined by holes/openings in the plate top and the plate bottom can be affixed to the plate top, directly or in combination with other components, and the plate bottom can serve as the bottom of the well. One or more assay reagents can be included in wells and/or assay domains of a plate. These reagents can be immobilized or placed on one or more of the surfaces of a well, preferably on the surface of an electrode and most preferably on the surface of a working electrode. The assay reagents can be contained or localized by features within a well, e.g., patterned dielectric materials can confine or localize fluids. The plate top preferably comprises a unitary molded structure made from rigid thermoplastic material such as polystyrene, polyethylene or polypropylene. The plate bottom preferably includes electrodes (e.g., working and/or counter electrodes) that comprise carbon, preferably carbon layers, more preferably screen-printed layers of carbon inks. In another preferred embodiment, the plate bottom includes electrodes comprised of a screen printed conducting ink deposited on a substrate.

A single well addressable plate includes a plate top having plate top openings and a plate bottom mated to the plate top to define wells of the single well addressable plate, the plate bottom comprising a substrate having a top surface with electrodes patterned thereon and a bottom surface with electrical contacts patterned thereon, wherein the electrodes and contacts are patterned to define a plurality of well bottoms of the single well addressable plate, wherein a pattern within a well bottom comprises: (a) a working electrode on the top surface of the substrate, wherein the working electrode is electrically connected to an electrical contact; and (b) a counter electrode on the top surface of the substrate, wherein the counter electrode is electrically connected with the electrical contact, but not with an additional counter electrode in an additional well of the single well addressable plate. Preferably, the electrodes and contacts of a single-well addressable plate are individually addressable.

A multi-well addressable plate includes a plate top having plate top openings and a plate bottom mated to the plate top to define wells of the multi-well addressable plate, the plate bottom comprising a substrate having a top surface with electrodes patterned thereon and a bottom surface with electrical contacts patterned thereon, wherein the electrodes and contacts are patterned to define two or more independently addressable sectors of two or more jointly addressable assay wells, each sector comprising two or more wells with: (a) jointly addressable working electrodes on the top surface of the substrate, wherein each of the working electrodes is electrically connected with each other and connected to at least a first of the electrical contacts; and (b) jointly addressable counter electrodes on the top surface of the substrate, wherein each of the counter electrodes is electrically connected with each other, but not with the working electrodes, and connected to at least a second of the electrical contacts. In one embodiment, the independently addressable sectors include less than 50% of the wells of the multi-well addressable plate, more preferably less than 20% of the wells of the multi-well addressable plate. The independently addressable sectors can comprise a 4×4 array of wells or a 2×3 array of independently addressable sectors. Alternatively, the independently addressable sectors can comprise one or more rows or one or more columns of wells.

A single-well or multi-well addressable plate can be a 4 well plate, 6 well plate, 24 well plate, 96 well plate, 384 well plate, 1536 well plate, 6144 well plate or 9600 well plate. The electrodes of either plate format comprise carbon particles and they can further comprise a printed conductive material, wherein one or more of the electrodes comprise a plurality of assay domains formed thereon. The plurality of assay domains can include at least four assay domains, preferably seven domains, and more preferably at least ten assay domains, and the plurality of assay domains can be defined by openings in one or more dielectric layers supported on the working electrodes. Plates that can be used in the apparatus are available from Meso Scale Discovery (Rockville, Md.; www.mesoscale.com) and include but are not limited to the following multi-well addressable plates (Meso Scale Discovery catalog numbers): L15XA-3, L15XB-3, L15AA-1, L15AB-1, L15SA-1, L15SB-1, L15GB-1, L45XA-3, L45XB-3, N45153A-2, N45153B-2, N45154A-2, and N45154B-2; and the following single-well addressable plates (Meso Scale Discovery catalog numbers): L55AB-1, L55SA-1, L55XA-1, and L55XB-1.

Accordingly, the apparatus measures luminescence from a multi-well plate by first detecting the plate type in the apparatus, e.g., by reading the bar code on the multi-well plate which includes plate configuration information, aligning the contact mechanism and imaging apparatus such that the interrogation zone or zones are directly under and in the imaging field of the imaging apparatus, and directing the selective application of potential by (a) electrically isolating each interrogation zone of the contact mechanism and selectively applying a potential only within a first zone (for a single-well addressable plate); or (b) electrically connecting two or more zone and selectively applying a potential within those two or more zone (for a multi-well addressable plate). If a multi-well addressable plate is being used in the apparatus, the imaging system and contact mechanism are aligned with an interrogation zone that corresponds to a grouping or sector of adjacent wells, e.g., a grouping of four adjacent wells, and the apparatus selectively applies a voltage to all wells of that sector. The apparatus then moves the plate via the plate translation stage to reposition the contact mechanism and imaging system with an additional interrogation zone that corresponds to an additional sector or grouping of wells, and selectively applies a voltage to the wells of that additional sector. If a single well addressable plate is being used in the apparatus, the imaging system and contact mechanism are aligned with an interrogation zone that corresponds to a grouping or sector of adjacent wells, e.g., a grouping of four adjacent wells, and the apparatus selectively applies a voltage to each well of that sector one at a time. Likewise, the plate is moved via the plate translation stage to reposition the contact mechanism and imaging system with an additional interrogation zone that corresponds to an additional sector of wells to interrogate each well of that additional sector one at a time.

In a specific embodiment, the apparatus can measure luminescence from a single well addressable plate or a multi-well addressable plate, wherein the apparatus includes:

(i) a plate type identification interface for identifying the plate type;

(ii) a plate translation stage for holding and translating the multi-well plate in the x-y plane;

(iii) a plate contact mechanism comprising a plurality of contact probes and positioned below the plate translation stage and within the range of motion of the stage, wherein the mechanism is mounted on a contact mechanism elevator that can raise and lower the mechanism to bring the probes into and out of contact with a bottom contact surface the plate when positioned on the translation stage;

(iv) a voltage source for applying potential through the contact probes to the plate; and (v) an imaging system positioned above the plate translation stage and in vertical alignment with the plate contact mechanism, wherein (a) the imaging system is configured to image a P×Q matrix of wells, the plate contact mechanism is configured to contact the bottom contact surface associated with the matrix and the plate translation stage is configured to translate a plate to position the matrix in alignment with the imaging system and plate contact mechanism;

(b) the apparatus is configured to sequentially apply a voltage to each well in the matrix of a single well addressable plate and image the matrix; and (c) the apparatus is configured to simultaneously apply a voltage to each well in the matrix of a multi-well addressable plate and image the matrix.

Preferably, the P×Q matrix is a 2×2 array of wells. The imaging system can collect a separate image for each sequential application of voltage to each well in the matrix of a single well addressable plate. The plate type identification interface can include a bar code reader, an EPROM reader, an EEPROM reader, or an RFID reader, or alternatively, the plate type identification interface comprises a graphical user interface configured to enable a user to input plate type identification information.

Therefore, a method for measuring luminescence from a single well addressable plate or a multi-well addressable plate using such an apparatus comprises:

(a) loading a plate on the plate translation stage;

(b) identifying the plate as being a single well or multi-well addressable plate;

(c) moving the plate translation stage to align a first P×Q matrix of wells with the plate contact mechanism and imaging system;

(d) raising the plate contact mechanism so that the contact probes on the contact mechanism contact the bottom contact surface associated with the P×Q matrix of wells;

(e) generating and imaging luminescence in the P×Q matrix by sequentially applying voltage to each well in the group while the group is imaged, if the plate is a single well addressable plate;

(f) generating and imaging luminescence in the P×Q matrix by simultaneously applying voltage to each well in the matrix while the matrix is imaged, if the plate is a multi-well addressable plate; and (g) repeating steps (c) through (f) for additional P×Q matrices in the plate.

The removable drawer may include a light source (e.g., an LED) located underneath the detection aperture and below the elevation of plate translation stage. In one embodiment, this light source or plurality of light sources are components of the plate contact mechanism. As described above in reference to the optical focusing mechanism, the light source(s) in the contact mechanism are used in connection with the optical focusing mechanism to adjust the contrast and focus of the light detector relative to a plate.

In an additional embodiment, one or more light source(s) can also be used in connection with fiducial holes or windows to correct for errors in plate alignment. Light from the light source is passed through the fiducials and imaged on the imaging apparatus so as to determine the correct for the alignment of the plate. Advantageously, plates formed from plate bottoms mated to a plate top (e.g., plates with screen printed plate bottoms mated to injection-molded plate tops as described in copending U.S. Applications 2004/0022677 and 2005/0052646) include fiducials patterned (e.g., screen printed) or cut into the plate bottom to correct for misalignment of the plate bottom relative to the plate top. In one specific embodiment, the plate top on such a plate includes holes (e.g., in the outside frame of the plate top) aligned with fiducials on the plate bottom to allow imaging of the fiducials. Accordingly, the imaging of light generated under a plate may be used to communicate the exact position of the plate to the image processing software and also to provide for a camera focus check. The plate may then be realigned using a two-axis positioning apparatus. Thus, the apparatus may process plates via a plate positioning method comprising: (1) providing a plate having light-path openings; (2) illuminating the plate from the bottom; (3) detecting light coming through light-path openings; and (4) optionally, realigning the plate.

In a preferred embodiment, the contact mechanism platform includes a first alignment feature 722 and the light detection subsystem comprises a camera positioned above the platform which is adjustable relative to the first alignment feature. Preferably, the first alignment feature is light source, e.g., an LED. The camera in the light detection subsystem is adjustable relative to the alignment feature in the x-y plane. The platform can further include a plurality of additional alignment features, e.g., at least one additional alignment feature in each quadrant, and the camera position is adjustable relative to each additional alignment feature. The additional alignment features can comprise a light source, e.g., an LED. Therefore, as described above, the apparatus may confirm proper alignment of the contact mechanism and the detection aperture using the optical focusing mechanism by: (1) illuminating the contact mechanism alignment features; (2) detecting light coming from the alignment features; and (4) optionally, realigning the plate translation stage, the light detector, and/or the contact mechanism. In one preferred embodiment, the apparatus confirms proper alignment of the contact mechanism before making contact with the plate and then the plate position is confirmed by detecting light coming from light-path openings in the plate and realigning the plate as needed.

As illustrated in FIG. 7(a)-(b), the height of the contact mechanism platform is adjustable because the platform further includes a shaft 723 driven by a gear mechanism 724. In one embodiment, the gear mechanism comprises a worm gear. In a preferred embodiment, the platform comprises a plate surface area sized to accommodate a microtitre plate, e.g., multi-well plate, and the platform further includes a spillage collection area surrounding the plate surface area to protect components of the drawer from accidental spills of fluid that may be contained within the multi-well plate.

Figure 8A:
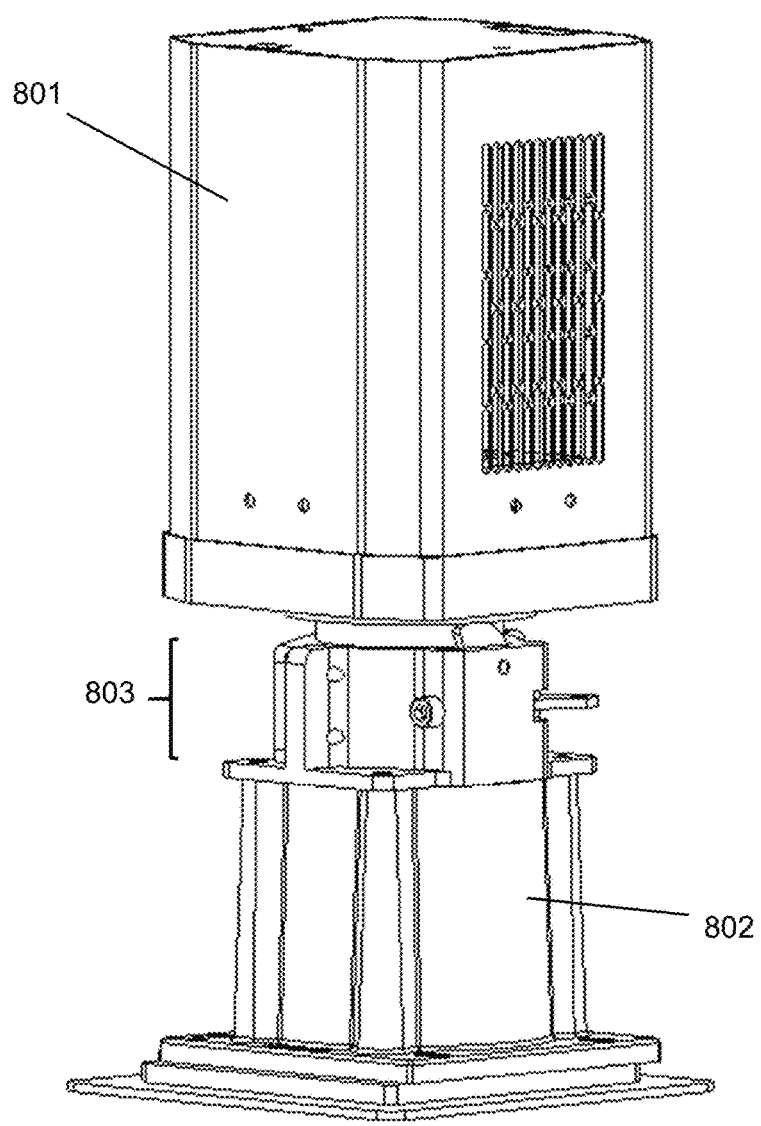
FIGS. 8(*a*)-(*c*) show various components of the light detection subsystem.
Figure 8B:
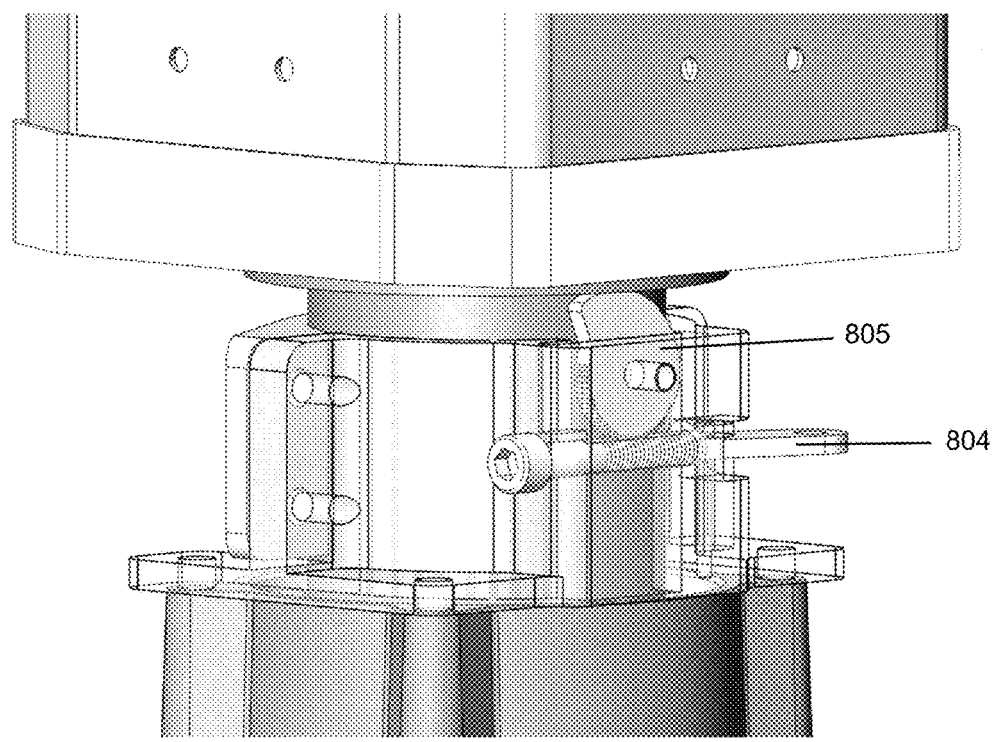
Figure 8C:
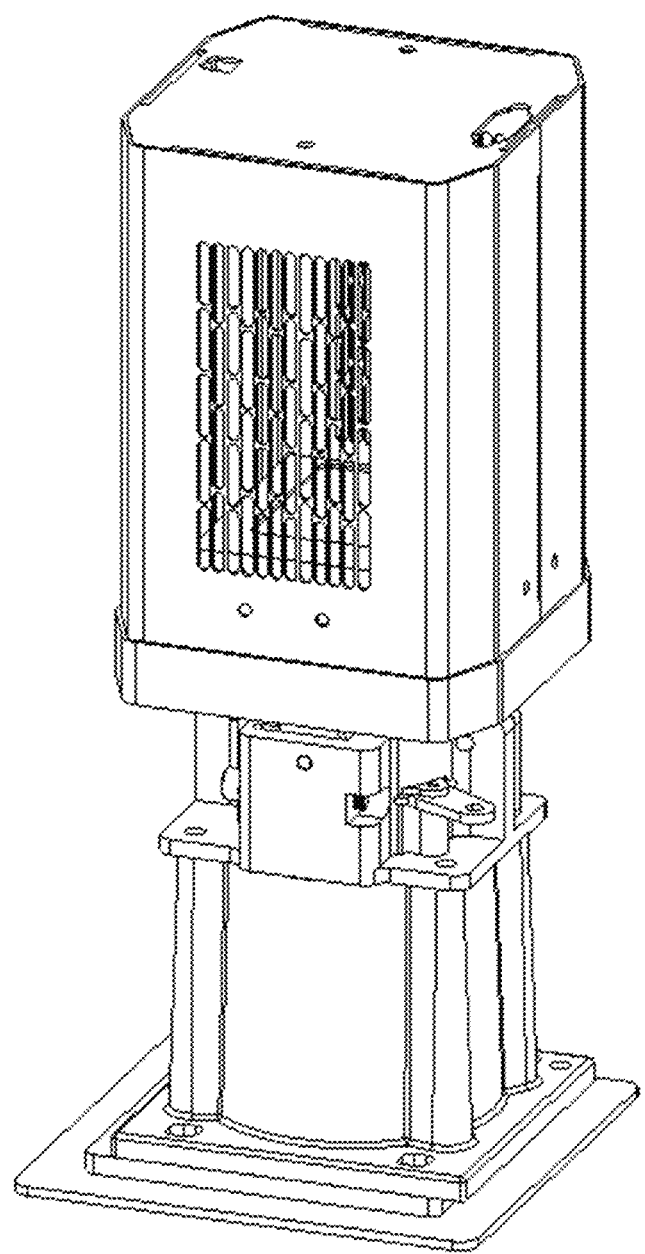

The light detection subsystem of the apparatus comprises a light detector that can be mounted to a detection aperture on the housing top via a light-tight connector or baffle. In certain embodiments, the light detector is an imaging light detector such as a CCD camera and it also includes a lens. A light detection subsystem is shown in FIG. 8(a). The subsystem includes a light detector housing 801 surrounding the light detector (not shown) and attached to the housing top via a cast component 802 that is bolted to the housing top over the detection aperture. Above the cast component sits a buckle or clamp 803 that includes a theta adjustment mechanism comprised of screw 804 and gear 805, illustrated in FIG. 8(b). The camera focusing mechanism is also configured to focus the camera in the x, y, and z directions as needed, either manually, via motorized elements, or both. The light detection subsystem further includes one or more light-tighting elements to prevent light leakage within the light detection subsystem or at the juncture between the light detection subsystem and the housing top. For example, molded rubber or other compressible materials can be sandwiched between joined components to prevent light leakage. In addition, the light detector housing includes one or more vents and/or cooling elements to cool the light detector within the housing. In one embodiment, the housing includes an intake vent and an exhaust vent, each positioned on the opposite ends of the housing. Additional vents can be positioned in the housing. In a preferred embodiment, the intake vent is sized to match a cooling fan positioned within the housing.

A lens, coupled to a camera, is used to provide a focused image of luminescence generated from plates in the light-tight enclosure. A diaphragm sealed to the lens and a detection aperture in the top of enclosure, and allows the imaging system to image light from enclosure while maintaining the enclosure in a light-tight environment protected from environmental light. Suitable cameras for use in the imaging system include, but are not limited to, conventional cameras such as film cameras, CCD cameras, CMOS cameras, and the like. CCD cameras may be cooled to lower electronic noise. Preferably, the lens is a high numerical aperture lens which may be made from glass or injection-molded plastic. The imaging system may be used to image one well or multiple wells of a plate at a time. The light collection efficiency for imaging light from a single well is higher than for imaging a group of wells due to the closer match in the size of the CCD chip and the area being imaged. The reduced size of the imaged area and the increase in collection efficiency allows for the use of small inexpensive CCD cameras and lenses while maintaining high sensitivity in detection.

Figure 9:
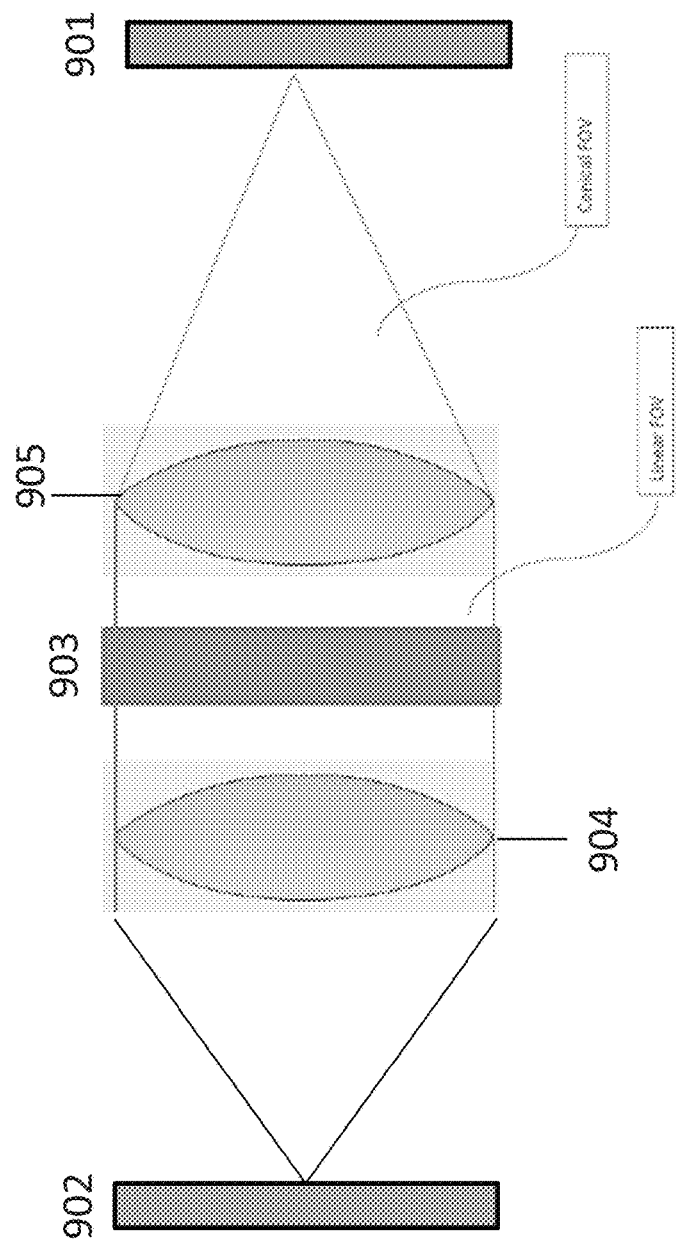
FIG. 9 shows one non-limiting embodiment of a lens configuration that can be used in the light detection subsystem.

If high resolution is not required, the sensitivity of the measurement can be improved by using hardware binning on the CCD during image collection, which effectively reduces the electronic read noise per unit area. Preferred binning depends on the field of view, demagnification, and size of the CCD pixels. In a preferred embodiment, the light detector comprises a camera with a CCD having 512×512 pixels, with each pixel size being 24×24 microns and a total area of 12.3×12.3 mm, and a lens with an image demagnification factor of 1.45×. For such detector and lens combination, 4×4 binning is preferred, resulting in a super-pixel size of approximately 100×100 microns, which translates to approximately 150 micron resolution in the object plane at the ECL electrode. Particularly advantageous, for their low cost and size, is the use of non-cooled cameras or cameras with minimal cooling (preferably to about −20° C., about −10° C., about 0° C., or higher temperatures). In a preferred embodiment, the light detection subsystem includes a lens assembly consisting of a series of lens elements (904 and 905) designed to produce a telecentric view of the imaged wells and an optical bandpass filter (903) in the optical path within the lens assembly such that the light rays passing through the filter are at substantially normal incidence with respect to the filter. In the embodiment illustrated in FIG. 9, the camera is provided a telecentric view of the imaged wells (901).

The housing top of the plate handling system further includes a plate stacker mounted on the housing top, above the plate introduction apertures, wherein the plate stackers are configured to receive or deliver plates to the plate elevators. The plate stacker can include a removable stacking nest configured to house a plurality of plates and prevent shifting of plates on the instrument, thereby coordinating the proper introduction of each plate in the stacking nest onto the plate elevator. In one embodiment, the stacking nest can accommodate at least 5 plates, and preferably at least 10 plates, and the stacking nest can accommodate a plate nesting extension element configured to further extend the capacity of the stacking nest. The plate elevator comprises a plate detection sensor, e.g., a capacitance sensor, and the stacker can also include a plate detection sensor, e.g., a capacitance, weight, or optical sensor.

A method is provided for using the apparatus for conducting measurements in multi-well plates. The plates may be conventional multi-well plates. Measurement techniques that may be used include, but are not limited to, techniques known in the art such as cell culture-based assays, binding assays (including agglutination tests, immunoassays, nucleic acid hybridization assays, etc.), enzymatic assays, colorometric assays, etc. Other suitable techniques will be readily apparent to one of average skill in the art.

Methods for measuring the amount of an analyte also include techniques that measure analytes through the detection of labels which may be attached directly or indirectly (e.g., through the use of labeled binding partners of an analyte) to an analyte. Suitable labels include labels that can be directly visualized (e.g., particles that may be seen visually and labels that generate an measurable signal such as light scattering, optical absorbance, fluorescence, chemiluminescence, electrochemiluminescence, radioactivity, magnetic fields, etc). Labels that may be used also include enzymes or other chemically reactive species that have a chemical activity that leads to a measurable signal such as light scattering, absorbance, fluorescence, etc. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the invention may benefit from or require a wash step to remove unbound components (e.g., labels) from the solid phase In one embodiment, a measurement done with the apparatus of the invention may employ electrochemiluminescence-based assay formats, e.g. electrochemiluminescence based immunoassays. The high sensitivity, broad dynamic range and selectivity of ECL are important factors for medical diagnostics. Commercially available ECL instruments have demonstrated exceptional performance and they have become widely used for reasons including their excellent sensitivity, dynamic range, precision, and tolerance of complex sample matrices. Species that can be induced to emit ECL (ECL-active species) have been used as ECL labels, e.g., (i) organometallic compounds where the metal is from, for example, the noble metals of group VIII, including Ru-containing and Os-containing organometallic compounds such as the tris-bipyridyl-ruthenium (RuBpy) moiety, and (ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by measuring ECL emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369; 6,214,552 and 5,589,136 and Published PCT Nos. WO99/63347; WO00/03233; WO99/58962; WO99/32662; WO99/14599; WO98/12539; WO97/36931 and WO98/57154, all of which are incorporated herein by reference.

In certain embodiments, plates adapted for use in electrochemiluminescence (ECL) assays are employed as described in U.S. Pat. No. 7,842,246. The apparatus of the invention can use plates that are configured to detect ECL from one well at a time or more than one well at a time. As described above, plates configured to detect ECL one well at a time or more than one well at a time include electrode and electrode contacts that are specifically patterned to allow application of electrical energy to electrodes in only one well at a time or more than one well at a time. The apparatus may be particularly well-suited for carrying out assays in plates containing dry reagents and/or sealed wells, e.g., as described in U.S. application Ser. No. 11/642,970 of Glezer et al.

In one embodiment, the method comprises: (a) introducing a plate to a plate stacker, (b) opening the light-tight door, (c) lowering the plate from the plate stacker to the lifting platform on the plate translation stage, (d) sealing the light-tight door, (e) translating the plate to position one or more wells under the light detector, (f) detecting luminescence from the one or more wells, (g) opening the light-tight door, (h) translating the plate to a position under a plate stacker, and (i) raising the plate to the plate stacker. In a preferred embodiment, the method also includes reading a plate identifier on the plate and identifying the plate configuration, translating the plate to position the one or more wells under the light detector, optionally imaging one or more alignment features on the contact mechanism and adjusting the position of the light detector relative to the contact mechanism, and selectively applying potential within one or more interrogation zones based on the plate configuration. The method may further comprise translating the plate carriage to position one or more additional wells under the light detector and detecting luminescence from the one or more additional wells. The method may also, optionally, comprise applying electrical energy to electrodes in one or more of the wells (e.g., to induce electrochemiluminescence).

ECL-based multiplexed testing is described in U.S. Publications 2004/0022677 and 2004/0052646 of U.S. application Ser. Nos. 10/185,274 and 10/185,363, respectively; U.S. Publication 2003/0207290 of U.S. application Ser. No. 10/238,960; U.S. Publication 2003/0113713 of U.S. application Ser. No. 10/238,391; U.S. Publication 2004/0189311 of U.S. application Ser. No. 10/744,726; and U.S. Publication 2005/0142033 of U.S. application Ser. No. 10/980,198.

A method is also provided for conducting assays for biological agents using the apparatus described herein. In one embodiment, the method is a binding assay. In another embodiment, the method is a solid-phase binding assay (in one example, a solid phase immunoassay) and comprises contacting an assay composition with one or more binding surfaces that bind analytes of interest (or their binding competitors) present in the assay composition. The method may also include contacting the assay composition with one or more detection reagents capable of specifically binding with the analytes of interest. The multiplexed binding assay methods according to preferred embodiments can involve a number of formats available in the art. Suitable assay methods include sandwich or competitive binding assays format. Examples of sandwich immunoassays are described in U.S. Pat. Nos. 4,168,146 and 4,366,241. Examples of competitive immunoassays include those disclosed in U.S. Pat. Nos. 4,235,601; 4,442,204; and 5,208,535 to Buechler et al. In one example, small molecule toxins such as marine and fungal toxins can be advantageously measured in competitive immunoassay formats.

Binding reagents that can be used as detection reagents, the binding components of binding surfaces and/or bridging reagents include, but are not limited to, antibodies, receptors, ligands, haptens, antigens, epitopes, mimitopes, aptamers, hybridization partners, and intercalaters. Suitable binding reagent compositions include, but are not limited to, proteins, nucleic acids, drugs, steroids, hormones, lipids, polysaccharides, and combinations thereof. The term "antibody" includes intact antibody molecules (including hybrid antibodies assembled by in vitro re-association of antibody subunits), antibody fragments, and recombinant protein constructs comprising an antigen binding domain of an antibody (as described, e.g., in Porter & Weir, J. Cell Physiol., 67 (Suppl 1):51-64, 1966; Hochman et al., Biochemistry 12:1130-1135, 1973; hereby incorporated by reference). The term also includes intact antibody molecules, antibody fragments, and antibody constructs that have been chemically modified, e.g., by the introduction of a label.

Measured, as used herein, is understood to encompass quantitative and qualitative measurement, and encompasses measurements carried out for a variety of purposes including, but not limited to, detecting the presence of an analyte, quantitating the amount of an analyte, identifying a known analyte, and/or determining the identity of an unknown analyte in a sample. According to one embodiment, the amounts the first binding reagent and the second binding reagent bound to one or more binding surfaces may be presented as a concentration value of the analytes in a sample, i.e., the amount of each analyte per volume of sample.

Analytes may be detected using electrochemiluminescence-based assay formats. Electrochemiluminescence measurements are preferably carried out using binding reagents immobilized or otherwise collected on an electrode surface. Especially preferred electrodes include screen-printed carbon ink electrodes which may be patterned on the bottom of specially designed cartridges and/or multi-well plates (e.g., 24-, 96-, 384- etc. well plates). Electrochemiluminescence from ECL labels on the surface of the carbon electrodes is induced and measured using an imaging plate reader as described in copending U.S. application Ser. Nos. 10/185,274 and 10/185,363 (both entitled "Assay Plates, Reader Systems and Methods for Luminescence Test Measurements", filed on Jun. 28, 2002, hereby incorporated by reference). Analogous plates and plate readers are now commercially available (MULTI-SPOT® and MULTI-ARRAY® plates and SECTOR® instruments, Meso Scale Discovery, a division of Meso Scale Diagnostics, LLC, Rockville, Md.).

In one embodiment, antibodies that are immobilized on the electrodes within the plates may be used to detect the selected biological agent in a sandwich immunoassay format. In another embodiment, microarrays of antibodies, patterned on integrated electrodes within the plates, will be used to detect the plurality of the selected biological agents in a sandwich immunoassay format. Accordingly, each well contains one or more capture antibodies immobilized on the working electrode of the plate and, optionally, in dry form or as separate components, e.g., in a kit, labeled detection antibodies and all additional reagents necessary for analysis of samples, and for carrying out positive and negative controls.

Patents, patent applications, publications, and test methods cited in this disclosure are incorporated herein by reference in their entirety. The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the claims.

PARTS LIST

| Reference No. | Part Name |
| --- | --- |
| 100 | Apparatus |
| 110 | Light detection system with light detectors |
| 120 | Plate handling system |
| 130 | Light tight enclosure |
| 231 | Housing |
| 232 | Housing top |
| 233 | Housing bottom |
| 234 | Housing front |
| 235 | Housing rear |
| 236, 237 | Plate introduction/ejection |
| 238 | Bar code reader |
| 240 | Removable drawer |

-continued

| Reference No. | Part Name |
| --- | --- |
| 400 | Plate elevator mechanism |
| 401, 402 | Plate lifting platform |
| 403 | Plate translation stage |
| 404 | Plate carriage with opening |
| 405, 406, 407 | Alignment pins |
| 408, 409, 410 | Alightment holes |
| 411 | Spring loaded pin |
| 412 | Hole in plate carriage 404 |
| 413 | Electrical contact mechanism on housing tip 232 |
| 414 | Companion electrical contact mechanism on drawer |
| 415 | X-Y Frame |
| 416, 417 | Alignment latches |
| 418, 419 | Alignment catches |
| 420 | Opening in carriage |
| 422, 424 | Rails |
| 426 | Multi-well plate |
| 501 | First stop |
| 502 | Plate clamp arm |
| 503 | Bracket |
| 504 | Leg |
| 506 | Leg |
| 507 | Ramp |
| 508 | Ramp |
| 509 | First latch member |
| 510 | Actuating rod |
| 510a | Extended portion of actuating rod |
| 511 | Pedal |
| 512 | Spring |
| 513 | Second Stop |
| 514 | Spring |
| 515 | Biased clamp |
| 515a | Extended portion of biased clamp |
| 515b | Biased end of biased clamp |
| 516 | Ejector |
| 522 | Skirt |
| 524 | Fulcrum |
| 526 | Sheath |
| 528, 530 | Ends of arm 502 |
| 531 | Pivot point |
| 532 | Spring for biased clamp 515 |
| 534 | Over-travel preventer |
| 536 | Conductive bottom surface |
| 701 | Platform |
| 702, 703, 704, 705 | Interrogation zones on platform 701 |
| 706, 707, 708, 709, 710, 711, 712, 713 | Working electrodes on platform 701 |
| 714, 715, 716, 717, 718, 719, 720, 721 | Counter electrodes on platform 701 |
| 722 | Aligning light outlet |
| 723 | Shaft |
| 724 | Gear mechanism |
| 725, 726, 727, 728 | Light outlets |
| 729 | Microprocessor |
| 730 | Power source |
| 731 | DAC |
| 732 | Low-pass filter |
| 733 | Low-pass filter |
| 734 | Current monitor |
| 736 | ADC |
| 737 | Power source |
| 738 | Multiplexer |
| 739 | LED |
| 740 | Bottom counter electrode |
| 742, 744 | Bottom working electrodes |
| 750 | Well working electrode |
| 752, 754 | Well counter electrodes |
| 760 | Bottom working electrode |
| 762 | Bottom counter electrode |
| 801 | Light detector housing |
| 802 | Cast component |
| 803 | Buckle or clamp |
| 804 | Screw |
| 805 | Gear |
| 901 | Imaged well |
| 902 | Camera |

-continued

| Reference No. | Part Name |
| --- | --- |
| 903 | Optical bandpass filter |
| 904 | Lens |
| 905 | Lens |

We claim:

1. An instrument comprising:
a contact platform, wherein the contact platform comprises a plurality of interrogation zones and each interrogation zone comprises at least one pair of working and counter electrical contact probes to conduct a voltage potential to the interrogation zone,
a controller operatively connected to a voltage source, wherein the voltage source is connectable to said at least one pair of working and counter electrical contact probes, and
a multiplexer connected to the controller and to the voltage source for selectively connecting the voltage source to the working electrical contact probe of a single interrogation zone or connecting the voltage source to the working electrical contact probes of more than one interrogation zone
wherein the counter electrical contact probes of more than one interrogation zone are electrically connected to the contact platform and to an electrical ground.

2. The instrument of claim 1, wherein the plurality of interrogation zones are arranged in a P×Q matrix.

3. The instrument of claim 1, wherein the interrogation zones are interrogated one zone at a time.

4. The instrument of claim 1, wherein more than one interrogation zone are interrogated at a time.

5. An instrument adapted to interrogate samples contained in a multi-well plate comprising:
a carriage frame configured to support the multi-well plate and the carriage frame is movable relative to a contact platform,
wherein the multi-well plate comprises a plurality of wells, wherein the wells are arranged in a M×N matrix, and
wherein the contact platform comprises a plurality of interrogation zones, wherein each interrogation zone comprises at least a pair of electrical contact probes to conduct a voltage potential to at least one well, and
a controller operatively connected to a motor to move the carriage frame relative to the contact platform and operatively connected to a voltage source, wherein the voltage source is connectable to the one or more pairs of electrical contact probes, and
a multiplexer connected to the controller and to the voltage source for selectively connecting the voltage source to the pair of electrical contact probes of a single interrogation zone or connecting the voltage source to at least one pair of electrical contact probes of more than one interrogation zone.

6. The instrument of claim 5, wherein the interrogation zones are arranged in a P×Q matrix, and wherein the M×N matrix is larger than the P×Q matrix.

7. The instrument of claim 5, wherein multi-well plate comprises bottom electrical contacts for each well on a bottom surface of the plate, wherein the bottom electrical contacts are adapted to contact the pairs of electrical contact probes on the contact platform.

8. The instrument of claim 7, wherein the multi-well plate further comprises internal electrodes in said wells connected to the bottom electrical contacts to conduct the voltage potential to within the wells.

9. The instrument of claim 8, wherein the at least a pair of electrical contact probes on the platform are connected to the bottom electrical contacts on the plate and to the internal electrodes in the wells to interrogate the wells.

10. The instrument of claim 5, wherein the electrical contact probes on the platform comprises a plurality of working contact probes that are selectively connected by the controller to the voltage source to determine the number of wells to interrogate.

11. The instrument of claim 10, wherein the working contact probes that are not connected are electrically isolated in the multiplexer.

12. The instrument of claim 10, wherein the electrical contact probes on the platform further comprises a plurality of counter contact probes that are electrically connected to at least one electrical ground.

13. The instrument of claim 12, wherein the bottom electrical contacts of the multi-well tray that are connected to the counter contact probe on the contact platform for at least one well are electrically isolated.

14. The instrument of claim 13, wherein the electrical contact probes are independently spring-loaded contact members.

15. The instrument of claim 12, wherein the plurality of counter contact probes on the platform is connected to a plurality of counter electrodes in the wells.

16. The instrument of claim 5, wherein the wells are interrogated one well at a time.

17. The instrument of claim 5, wherein more than one well are interrogated at a time.

18. A focusing mechanism for an optical sensor comprising at least a higher, middle and lower patterned surface spaced apart from the optical sensor;
wherein the middle patterned surface is aligned to a target surface to be focused by the optical sensor;
wherein a first distance between the higher and middle patterned surfaces and a second distance between the middle surface and lower patterned surface are substantially equal,
wherein the optical sensor and the patterned surfaces are moved relative to each other until a difference between a first and a second contrast value difference is less than a predetermined value; and
an illuminating source positioned to project light through the higher, middle and lowered patterned surfaces toward the optical sensor.

19. The focusing mechanism of claim 18, wherein the target surface comprises a reference surface of a platform that selectively conducts electricity to samples that are interrogated by the optical sensor.

20. The focusing mechanism of claim 19, wherein the middle patterned surface is aligned to the reference surface of the platform by a predetermined amount.

21. The focusing mechanism of claim 18, wherein the target surface comprises a bottom surface of a tray carrying at least one sample to be interrogated by the optical sensor.

22. The focusing mechanism of claim 21, wherein the middle patterned surface and the bottom surface of the tray are aligned to substantially a same planar level.

23. A method for focusing an optical sensor to a spaced apart platform comprising the steps of
a. providing at least a higher, middle and lower patterned surface, wherein the middle patterned surface and the platform are aligned to each other and wherein a first distance between the higher and middle patterned surfaces and a second distance between the middle surface and lower patterned surface are substantially equal;

b. obtaining a first contrast value difference between the higher and middle patterned surfaces with the optical sensor;

c. obtaining a second contrast value difference between the middle and lower patterned surfaces with the optical sensor;

d. comparing the first and second contrast value differences.

24. The method of claim 23 further comprising the step of (e) adjusting a distance between the optical sensor and the platform and repeating steps (b) to (d) until a difference between the first and second contrast value differences is determined to be less than a predetermined value.

25. The method of claim 24, wherein the predetermined value is less than about ±4.0.

26. The method of claim 23, wherein the middle patterned surface is aligned substantially to a same planar level as a bottom surface of a tray carrying at least one sample to be interrogated by the optical sensor.

27. The method of claim 26, wherein the platform comprises a plurality of electrode contact probes that contact the bottom surface of the tray to conduct electricity to the at least one sample.

28. The method of claim 23, wherein the higher, middle and lower patterned surfaces are located on parallel planar planes.

* * * * *